United States Patent [19]
Lessey

[11] Patent Number: 5,478,725
[45] Date of Patent: Dec. 26, 1995

[54] $\alpha_v\beta_3$ INTEGRIN AS A PREDICTOR OF ENDOMETRIOSIS

[75] Inventor: Bruce A. Lessey, Hillsborough, N.C.

[73] Assignee: University of Pennsylvania, Philadelphia, Pa.

[21] Appl. No.: 155,435

[22] Filed: Nov. 19, 1993

Related U.S. Application Data

[63] Continuation-in-part of Ser. No. 897,706, Jun. 12, 1992, Pat. No. 5,279,941.
[51] Int. Cl.[6] .................. G01N 33/537; G01N 33/543; G01N 33/577
[52] U.S. Cl. .................. 435/7.21; 435/960; 436/518; 436/519; 436/536; 436/548; 436/65
[58] Field of Search .................. 435/7.21, 960; 436/510, 518, 519, 536, 548, 65, 814; 530/388.22

[56] References Cited

U.S. PATENT DOCUMENTS 5,057,604  10/1991  Borwn .................. 530/387

OTHER PUBLICATIONS

Albelda et al., "EndoCAM: a novel endothelial cell–cell adhesion molecule", *J Cell Biol.* 110:1227–37, 1990.
Albelda et al., "Integrins and other cell adhesion molecules," *FASEB J.* 4:2868–2880, 1990.
American Fertility Society: Revised American Fertility Society Classification of Endometriosis: 1985. Fertil. Steril., 43:351–352, 1985.
Anderson T.; "Biomolecular Markers for the Window of Uterine Receptivity" in Blastocyst Implantation, Yoshinaga, K. ed., Serono Symposia, 219–224 (1989).
Anderson, T. et al, "Uterine Receptivity in the Primate" Development of Preimplantation Embryos and Their Environment, pp. 389–399 (1989).
Bancroft et al., Minimal/Mild Endometriosis and Infertility. A Review, Br. J. Obstet. Gynaecol., 96:454, 1989.
Barbieri et al., Evaluation of a Serological Test for the Diagnosis of Endometriosis using a Monoclonal Antibody OC–125, SGI Annual Meeting 1985; Mar.:331P.
Bennett et al., "Inhibition of fibrinogen binding to stimulated human platelets by a monoclonal antibody," *PNAS* 80:2417, 1983.
Brass et al., "Effect of Calcium on the Stability of the Platelet Membrane Glycoprotein IIb–IIIa Complex," *J. Biol. Chem.* 260:7876, 1985.
Buck et al., "Integrin, a transmembrane glycoprotein complex mediating cell–substratum adhesion," *J. Cell Sci. Suppl.* 8:231–250, 1987.
Budwit–Novotny et al., Immunohistochemical Analyses of Estrogen Receptor in Endometrial Adenocarcinoma Using a Monoclonal Antibody, Cancer Res., 46:5419–5425, 1986.
Burridge et al., "Focal adhesions: Transmembrane junctions between the extracellular matrix and the cytoskeleton," *Ann. Rev. Cell Biol.* 4:487–525, 1988.
Davies et al., "The Osteoclast Functional Antigen, Implicated in the Regulation of Bone Resorption, Is Biochemically Related to the Vitronectin Receptor," *J. Cell Biol.* 109:1817, 1989.
Fay, T. N.; "Human Endometrial Peptides: A Review of Their Potential Role in Implantation and Placentation" Human Reproduction vol. 6, No. 9 1311–1326 (1991).
Fedele et al., Structural and Ultrastructural Defects in Preovulatory Endometrium of Normo–Ovulating Infertile Women with Minimal or Mild Endometriosis, Fertil. Steril., 53:989, 1990.
Getzenberg et al., "The tissue matrix: Cell dynamics and hormone action," *Endocrine Rev.* 11:399–417, 1990.
Hahn et al., Experimental Evidence for Failure to Implant as a Mechanism of Infertility Associated with Endometriosis, Am. J. Obstet. Gynecol., 155:1109, 1986.
Hasson, Incidence of Endometriosis in Diagnostic Laparoscopy, J. Reprod. Med., 16:135, 1976.
Hemler, "VLA proteins in the integrin family: structures, functions and their role on leukocytes," *Annu. Rev. Immunol.*, 8:365–400, 1990.
Hertig, A. T., et al. E.C. "A Description of 34 Human Ova within the First 17 Days of Development"; *Am. J. Anat.* 98:435–493 (1956).
Hornstein et al., Menstrual Cyclicity of CA–125 in Patients with Endometriosis, Fertil. Steril., 58:279, 1992. Aug.
Kao et al., "The human villous cytotrophoblast: Interactions with extracellular matrix proteins, endocrine function, and cytoplasmic differentiation in the absence of syncytium formation," *Development Biol.* 130: 693–702, 1988.
Kohler and Milstein, "Continuous cultures of fused cells secreting antibody of predefined specificity," *Nature* 256:495, 1975.

(List continued on next page.)

Primary Examiner—Toni R. Scheiner
Assistant Examiner—Nancy J. Parsons
Attorney, Agent, or Firm—Woodcock Washburn Kurtz Mackiewicz & Norris

[57] ABSTRACT

Methods of screening for endometriosis comprise obtaining a sample of endometrium selected from menstrual cycle day 20 to 24, identifying the endometrial sample as nulliparous, contacting the endometrium with a monoclonal antibody for $\beta_3$ integrin, assaying for $\beta_3$ integrin and correlating the absence of $\beta_3$ integrin with endometriosis, wherein the endometrium is identified as mild/minimum endometriosis. A method of using monoclonal antibodies to screen for endometriosis is also within the scope of the invention. Methods for detecting receptivity of mammalian endometrium to embryo implantation comprising obtaining a sample of the endometrium, contacting the endometrium with a monoclonal antibody for $\beta_3$ and detecting $\beta_3$ in the endometrium. The invention also provides for methods of diagnosing infertility in a mammal and methods of detecting the window of embryo implantation in endometrium. Methods of in vitro fertilization, methods of preventing embryo implantation and a method of monitoring endometrial maturation are also within the scope of the present invention. Diagnostic kits useful in the practice of the methods of the invention are also provided.

8 Claims, 11 Drawing Sheets

OTHER PUBLICATIONS

Kurzrock R, et al. "LIF: Not Just a Leukemia Inhibitory Factor" Endocrine Reviews vol. 12, pp. 208–217 (1991).

Laemmli, "Cleavage of structural proteins during assemby of the head of bacteriophase T4," *Nature* 227:680–685, 1970.

Lessey et al., Abstract from 2nd International Conference on The Extracellular Matrix of the Reproductive Tract, May 1992.

Lessey et al., Abstract #401 from 38th Annual Meeting of the Society for Gynecological Invesitgation, Mar. 1991.

Lessey et al., "Integrin Adhesion Molecules in the Human Endometrium," *J. Clin. Invest.*, 90:188, 1992. Jul.

Lowry et al., "Protein measurement with the Folin phenol reagent," *J. Biol. Chem.* 193:265–271, 1951.

Martel, D.; "Scanning Electron Microscopy of the Uterine Luminal Epithelium as a Marker of the Implantation Window" in *Blastocyst Implantation*, Yoshinaga, K. ed. Serono Symposia 225–230 (1989).

Mauritisen, EGRET. Statistics and Epidemiology Research Corporation Software. Seattle, Wash., 1990.

Metz, Basic Principles of ROC Analysis, Sem. Nuclear Med., 8:283–298, 1978.

Muscato et al., Sperm Phagocytosis by Human Peritoneal Macrophages: A Possible Cause of Infertility in Endometriosis, Am. J. Obstet. Gynecol., 144:503, 1982.

Navot, D. et al. "Preparation of the Human Endometrium for Implantation", *Ann. N.Y. Acad. Sci.* 622:212–219 (1991).

Navot, D. M. "The Window of Embryo Transfer and the Efficiency of Human Conception in vitro", *Fertil. Steril.* 55:114–117 (1991).

Navot, D. et al. "An Insight into Early Reproductive Processes Through the In Vivo Model of Ovum Donation" *J. Clin. Endocrinol.* 72:408–414 (1991).

Noyes et al., "Dating the endometrial Biopsy," *Fertil. and Sterility* 1:3–8, 1950.

Peterson et al., Laparoscopy of the infertile Patient, Obstet. Gynecol., 36:363–367, 1970.

Pierschbacher et al., "Synthetic Peptide with Cell Attachment Activity of Fibronectin", *PNAS* 80:1224, 1983.

Pope et al., Uterine Asynchrony: A cause of Embryonic Loss, Biol. Reprod., 39:999, 1988.

Psychoyos A. et al. "Embryo–Endometrial Interactions at Implantation" Implantation of the Human Embryo Academic Press Inc. 195–209 (1985).

Rogers and Murphy, "Uterine Receptivity for Implantation: Human Studies", in *Blastocyst Implantation* 1989, Yoshinaga, K. ed., Serono Symposia.

Ruoslahti E. et al. "New Perspectives in Cell Adhesion: RGD and Integrins" *Science* 238:491–497 (1987).

Satyaswaroop et al., "Isolation and culture of human endometrium glands," *J. Clin. Endocr. and Metab.* 48:639–641, 1979.

Schlafke Sandra, et al. "Cellular Basis of Interaction Between Trophoblast and Uterus at Implantation" *Biology of Reproduction* 12, 41–65 (1975).

Simon C, et al. "A Novel Immune Mediator Prevents Embryonic Implantation" Annual Mtg of Am. Fert. Soc. Montreal, S2–Abst O–3 (1993).

Tabibzadeh, "Patterns of Expression of Integrin Molecules in Human Endometrium Throughout the Menstrual Cycle", *Hum. Reprod.* 7:876, 1992.

Tabibzadeh Siamak "Immunoreactivity of Human Endometrium: Correlation with Endometrial Dating" Fertility and Sterility, 54:624–631, No. 4 Oct. (1990).

Vanderpuye et al., "A Vitronectin–receptor–related molecule in human placental brush border membranes", *Biochem. J.* 280:9–17, 1991.

Wilcoxon, Individual Comparisons by Ranking Methods. Biometrics Bull, 1:80–85, 1945.

Yovich et al., Hormonal Profiles and Embryo Quality in Women with Severe Endometriosis Treated by In Vitro Fertilization and Embryo Transfer, Fertil. Steril., 50:308, 1988.

FIG. IA
FIG. IB
FIG. IC
FIG. ID
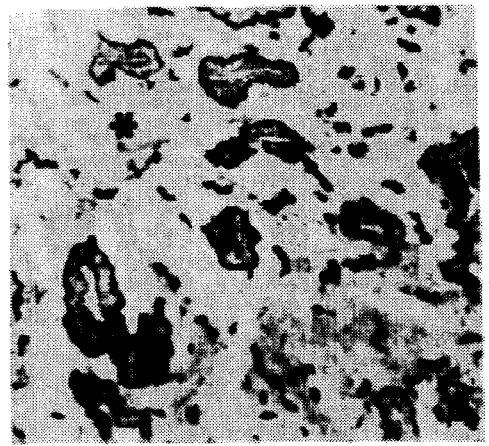
FIG. IE
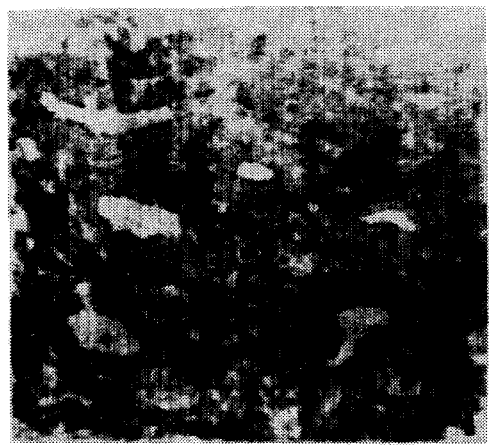
FIG. IF

$\alpha_v\beta_3$ INTEGRIN AS A PREDICTOR OF ENDOMETRIOSIS

REFERENCE TO GOVERNMENT GRANTS

This work was supported in part by research grants from the Biomedical Research Support Grant Program, Division of Research Resources, the National Institutes of Health, grant numbers B.R.S.B. S07-RR-05415-29 and HD30476-1. The United States Government may have certain rights in this invention.

REFERENCE TO APPLICATIONS

This application is a continuation in part of application Ser. No. 897,706, filed June 12, 1992, now U.S. Pat. No. 5,279,941.

BACKGROUND OF THE INVENTION

Over the past decade, investigators have come to recognize the importance of the extracellular matrix (ECM) in directing the growth, differentiation and function of the overlying epithelium. Getzenberg et al., "The Tissue Matrix: Cell Dynamics and Hormone Action", *Endocrine Rev.* 1990, 11:399. The interaction between cell and extracellular matrix (or substratum) is mediated by several classes of cell adhesion molecules, one of the most important being the integrins. Albelda et al., "Integrins and Other Cell Adhesion Molecules", *FESEB J.* 1990, 4:2868. Buck et al., "Integrin, a Transmembrane Glycoprotein Complex Mediating Cell-Substratum Adhesion", *J. Cell Sci. Suppl.* 1987, 8:231. This diverse family of glycoprotein receptors is expressed on the cell membrane as heterodimeric $\alpha$ and $\beta$ integrin subunits and is involved in both cell-cell and cell-substratum adhesion. Specific recognition and binding of extracellular matrix (ECM) components such as fibronectin (FN), laminin (LM) and collagen (Col) transmit information to the cytoskeletal structure, an interaction which may have major roles in promoting hormone responsiveness and genomic activation. Burridge et al., "Focal Adhesions: Transmembrane Junctions Between the Extracellular Matrix and the Cytoskeleton", *Ann. Rev. Cell. Biol.* 1988, 4:487 and Getzenberg et al. supra.

Although extensive information exists about specific integrin proteins, for example, Hemler, M. E. "VLA Proteins in the Integrin Family: Structures, Functions and Their Role on Leukocytes", *Annu. Rev. Immunol.* 1990, 8:365, little is known concerning the distribution of these receptors in the female reproductive tract. In the uterus, the endometrium, composed of glandular epithelium and associated mesenchyme (stroma), maintains complex temporal and spatial functions in response to the cyclic hormonal milieu. While Tabibzadeh reported that dynamic alterations in integrin expression accompany the other histologic changes that temporally mark the menstrual cycle, Tabibzadeh, S., "Patterns of Expression of Integrin Molecules in Human Endometrium Throughout the Menstrual Cycle", *Hum. Reprod.* 1992, 7:876, the search for morphological or biochemical markers for uterine receptivity has been unsuccessful to date as reported by Rogers and Murphy, "Uterine Receptivity for Implantation: Human Studies", in *Blastocyst Implantation* 1989, Yoshinaga, K. ed., Serono Symposia, p. 231. Once such markers are identified, their role in endometrial phenomena including embryo implantation, fertility, contraception and endometrial maturation and receptivity can likely also be identified. Thus, as some integrins appear to meet the criteria for markers of receptivity there is a great need for methods of detecting integrin cell adhesion molecules in endometrium.

Asynchrony between uterine and embryonic development has been suggested as a cause of pregnancy loss, on the basis of a misalignment between endometrial and embryonic receptivity, see Pope, et al., "Uterine Asynchrony: A cause of Embryonic Loss", *Biol. Reprod.* 1988, 39:999.

The relationship between minimal endometriosis and nulliparity and infertility remains controversial. While many cogent arguments exist to support this association, many clinicians today still do not believe that minimal or mild forms of the disease are detrimental to a couple's fertility. Several studies comparing women with normal endometrium to women with mild or minimal endometriosis have demonstrated a decrease in cycle fecundity, such as success rates in donor programs, IVF, or GIFT, supported by animal models. One reason for this lack of acceptance is the finding of many studies that expectant management yields pregnancy rates as high as most currently used treatments.

Of the many mechanisms suggested to explain the decline in cycle fecundity of endometriosis patients, a defect in uterine receptivity has received perhaps the least attention. Fedele reported specific changes in the native endometrium in women with severe endometriosis, Fedele, L., et al., "Structural and Ultrastructural Defects in Preovulatory Endometrium of Normo-Ovulating Infertile Women with Minimal or Mild Endometriosis", *Fertil. Steril.* 1990, 53:989. Yovich suggested that severe endometriosis was associated with a defect in implantation, based on IVF-ET experience, see Yovich et al., "Hormonal Profiles and Embryo Quality in Women with Severe Endometriosis Treated by In Vitro Fertilization and Embryo Transfer", *Fertil. Steril.* 1988, 50:308. There is data from studies in the rabbit to suggest that implantation is adversely affected by surgically induced endometriosis, and that the effect is mediated by the peritoneal fluid, see Hahn et al., "Experimental Evidence for Failure to Implant as a Mechanism of Infertility Associated with Endometriosis", *Am. J. Obstet. Gynecol.* 1986, 155:1109.

Endometriosis is a disorder that affects an estimated 2–5% of the general fertile female population, yet its prevalence in infertile women approaches 30–50%, Peterson et al., "Laparoscopy of the infertile Patient", *Obstet. Gynecol.* 1970, 36:667. While many affected women may have no symptoms, others suffer from dysmenorrhea (painful, difficult menstruation), dyspareunia (pain during intercourse), menstrual disturbances and infertility. That mild or minimal endometriosis is associated with infertility has been suggested by numerous studies, Hasson H. M., "Incidence of Endometriosis in Diagnostic Laparoscopy", *J. Reprod. Med.* 1976, 16:135 and has been recently reviewed, Bancroft, et al., "Minimal/Mild Endometriosis and Infertility. A Review", *Br. J. Obstet. Gynaecol.* 1989, 96:454. The mechanism by which minimal endometriosis causes infertility remains uncertain. Adverse effects on folliculogenesis, ovulation, ovum transport, fertilization, sperm quality, embryos, luteal phase function, and an increase in spontaneous abortion rates have all been postulated. These effects may be mediated by elaboration of peritoneal factors such as prostaglandins, cytokines, and growth factors; activation of peritoneal macrophages, or alterations in immune function such as decreased activity of natural killer cells. Kurzrock et al., "LIF: Not Just a Leukemia Inhibitory Factor", *Endo. Rev.* 1990, 12:208. A few authors have suggested that uterine receptivity to the embryo might be primarily affected by the presence of endometriosis, Muscato, et al., "Sperm Phagocytosis by Human Peritoneal Macrophages: A Possible Cause of Infertility in Endometriosis", *Am. J. Obstet. Gynecol.* 1982, 144:503 and Yovich et al., supra; and limited data from surgically induced endometriosis in animal models support this hypothesis, Hahn, et al., supra. Further, structural abnormalities have been described in the endometrium of women with endometriosis compared to normal fertile controls, Fedels, et al., supra.

Numerous approaches have been investigated to identify women with endometriosis using non-surgical means. Serum markers such as OC-125, (Barbieri, et al. "Evaluation of a Serological Test for the Diagnosis of Endometriosis using a Monoclonal Antibody OC-125", SGI Annual Meeting 1985; March:331P (abstract)) is increased in women with endometriosis, though the overlap with normal or other disease states severely limits its utility as a diagnostic test, Hornstein, et al., "Menstrual Cyclicity of CA-125 in Patients with Endometriosis", *Fertil. Steril.* 1992, 58:279 Further, given its graduated elevations with severity of disease, OC-125 has little utility in cases of minimal or mild endometriosis. Other modalities such as MRI or ultrasound also have their highest sensitivity in the presence of advanced endometriosis. To date, no method other than laparoscopy has been demonstrated to provide proven efficacy for the diagnosis of minimal or mild stages of endometriosis.

While uterine receptivity remains a poorly understood phenomenon, the initial attachment of embryo to maternal uterine lining is thought to be a critical step in the implantation process. A window of implantation has been defined by descriptive studies from the 1950s as well more recent studies using advanced reproductive technologies, Hertig et al., 1956 and Navot et al., 1992. The presence of an integrin cell adhesion molecule that reliably appears on the endometrial epithelial cells after day 19 of the normal menstrual cycle, corresponds to this putative time of implantation, Lessey, et al., "Integrin Adhesion Molecules in the Human Endometrium", *J. Clin. Invest.* 1992, 90:188. The expression of this integrin, the $\alpha_v\beta_3$ vitronectin receptor, is delayed in women with maturational delay of the endometrium, (where endometrial histology is delayed or retarded because of inadequate hormone levels or decreased response to existing levels of hormones) as well. As it has been suggested by some that infertility due to endometriosis may reflect a defect in uterine receptivity, it is of interest to investigate the expression of this protein in the endometria of women with infertility. The use of integrins as diagnostic tools to investigate uterine receptivity proves to be of significant value in identifying affected individuals and assist in understanding the etiology of infertility associated with mild forms endometriosis.

SUMMARY OF THE INVENTION

The present invention is directed to methods of predicting endometriosis. Methods of using monoclonal antibodies to $\beta_3$ integrin are also within the scope of the invention.

The methods of predicting endometriosis comprise obtaining a sample of endometrium selected from menstrual cycle day 20 to 24, identifying the endometrial sample as nulliparous, contacting the sample with a monoclonal antibody specific for $\beta_3$ integrin, assaying for $\beta_3$ integrin in the sample, and correlating the absence of $\beta_3$ integrin with endometriosis, wherein the endometrium is identified as mild/minimal endometriosis. The present invention is also useful in predicting endometriosis in the general infertile female population.

The methods of using monoclonal antibodies to $\beta_3$ integrin to predict endometriosis comprise obtaining a sample of endometrium selected from menstrual cycle day 20 to 24, contacting the sample with a monoclonal antibody specific for $\beta_3$ integrin, assaying for $\beta_3$ in the sample, correlating the absence of $\beta_3$ with endometriosis, wherein the endometrium is identified as nulliparous or having mild/minimal endometriosis.

The present invention is directed to methods of detecting receptivity of endometrium to embryo implantation by detecting the $\beta_3$ subunit of the $\alpha_v/\beta_3$ integrin in endometrium with a monoclonal antibody.

Methods of diagnosing fertility and methods of monitoring endometrial maturation in a mammal are also provided by monitoring the appearance of the $\beta_3$ subunit of integrin in endometrium from a plurality of stages of the endometrial cycle. This is preferably done with a monoclonal antibody.

The present invention also provides methods of detecting the optimal window of embryo implantation in the endometrium by detecting the $\beta_3$ subunit of integrin in an endometrial sample, preferably with a monoclonal antibody.

Further aspects of the invention include methods of preventing embryo implantation by contacting the $\beta_3$ subunit of integrin in the endometrium with neutralizing Fab antibody fragments to $\beta_3$. Methods of in vitro fertilization are also embodiments of the invention. These comprise detecting the $\beta_3$ subunit of integrin in an endometrial sample, fertilizing an egg in vitro, and introducing the zygote into the uterus having endometrial tissue expressing the $\beta_3$ subunit.

Contraceptive and diagnostic kits are also contemplated hereby.

These and other aspects of the invention will become more apparent from the following detailed description when taken in conjunction with the following figures.

BRIEF DESCRIPTION OF THE FIGURES

FIGS. 1A–1F depict immunoperoxidase staining of normal endometrium. The photomicrographs depict the pattern of distribution for six different integrins that do not appear to change throughout the menstrual cycle. Dark areas represent positive staining, light areas represent absence of stain (absence of specific integrin subunit). Immunohistochemical staining of the collagen/laminin receptor subunits: $\alpha_2$(A), $\alpha_3$(B), $\alpha_6$(C), and $\beta_4$(D) shows prominent staining of epithelium (←) and microvessels (←) without significant stromal staining (*) for $\alpha_2$, $\alpha_3$, and $\beta_4$. Note basolateral staining $\alpha_6$ and basal staining for $\beta_4$. Staining for fibronectin receptor subunits $\alpha_4$(E) is not present in the proliferative stage, $\alpha_5$(F) shows predominant mesenchyme staining (*) with decreased epithelial staining (←). The immunoreactions (areas of dark staining) were developed by avidin-biotin-peroxidase complex using diaminobenzadine as a chromogen. For greater sensitivity, no counterstain was applied. Magnification: 125X.

DESCRIPTION OF PREFERRED EMBODIMENTS

Figure 2A:
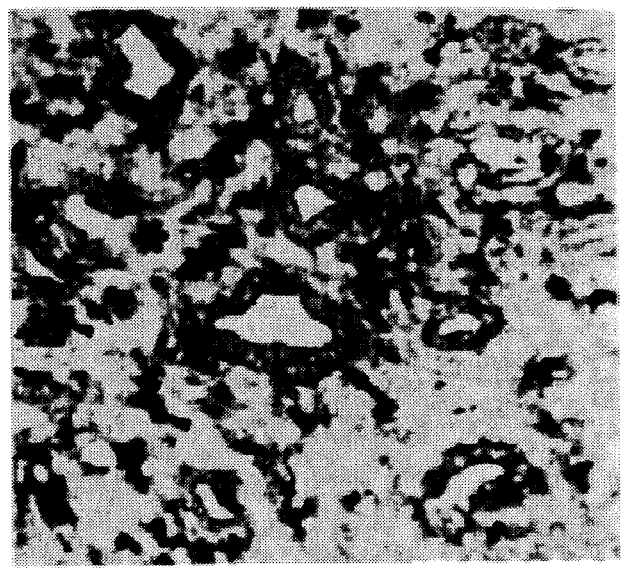
FIGS. 2A–2C show photomicrographs of the immunohistochemical staining for the integrin subunit $\alpha_1$ in proliferative vs. secretory endometrium. The staining in the glandular epithelium (←) was largely absent in the proliferative phase (A), and pronounced in all sections after menstrual cycle day 14 (B; day 20 endometrium). The microvasculature (←) staining was also pronounced, and did not change throughout the menstrual cycle. The staining noted in secretory endometrial glands was significantly higher than that of background (C). Magnification: 125X.

The present invention is directed to methods of predicting endometriosis. Methods of using monoclonal antibodies to $\beta_3$ integrin are also within the scope of the invention.

The methods of predicting endometriosis comprise obtaining a sample of endometrium selected from menstrual cycle day 20 to 24, identifying the endometrial sample as nulliparous, contacting the sample with a monoclonal antibody specific for $\beta_3$ integrin, assaying for $\beta_3$ integrin in the sample, and correlating the absence of $\beta_3$ integrin with endometriosis, wherein the endometrium is identified as mild/minimal endometriosis. The sample of endometrium is preferably selected from menstrual cycle days 20 to 24, more preferably menstrual cycle days 20 to 23, even more preferably menstrual cycle day 22. Cycle days 20–24 correspond to post-ovulatory days 6–10. The present invention is also useful in predicting endometriosis in the general infertile female population.

The methods of using monoclonal antibodies to $\beta_3$ integrin to predict endometriosis comprise obtaining a sample of endometrium, contacting the sample with a monoclonal antibody specific for $\beta_3$ integrin, assaying for $\beta_3$ in the sample, correlating the absence of $\beta_3$ with endometriosis, wherein the endometrium is identified as nulliparous or having mild/minimal endometriosis.

The present invention is directed to methods of detecting receptivity of mammalian endometrium including obtaining a sample of endometrium, contacting the sample with a monoclonal antibody for the $\beta_3$ subunit of integrin and detecting the $\beta_3$ subunit.

For purposes of the present invention, the $\beta_3$ subunit may be $\beta_3$ alone or $\beta_3$ in combination with another integrin subunit, $\alpha_v$ for example.

As used herein integrin is defined as a diverse class of glycoprotein receptors expressed on the cell membrane. Integrins are cell adhesion molecules of the immunoglobulin superfamily. Integrins are composed of heterodimeric $\alpha$ and $\beta$ subunits and are involved in cell—cell and cell—extracellular matrix adhesion. The integrin family is a broadly distributed group of receptors composed of non-covalently associated α/β heterodimer pairs that mediate leukocyte—leukocyte and leukocyte—endothelial cell adhesion, as well as cellular interactions with extracellular matrix components such as collagen, laminin, fibrinogen and fibronectin, and cell-cell interaction in organized tissues.

While integrins are found on virtually all cell types (the exception being red blood cells), expression of integrin subunits varies from cell type to cell type. In human uterine endometrium, as determined herein, glandular epithelial cells express primarily $\alpha_2$, $\beta_3$ and $\alpha_6$ integrin subunits, which are collagen laminin receptors. Stromal cells express predominantly $\alpha_5$, a fibronectin receptor. The presence of $\alpha_1$ on glandular epithelial cells is menstrual cycle specific, found only during the secretory phase. Expression of both subunits of the vitronectin receptor, $\alpha_v/\beta_3$, also undergoes menstrual cycle specific changes on endometrial epithelial cells. The expression of $\alpha_v$ increases throughout the menstrual cycle while the $\beta_3$ subunit appears abruptly on menstrual cycle day 20 on luminal and glandular epithelial cells. $\alpha_4$ expression was also found to turn off on day 23. Assaying for the expression of $\beta_3$ with monoclonal antibody SSA6 revealed $\beta_3$ expression from day 20 onward into the cycle. $\alpha_4$ expression begins on day 14 and is no longer expressed after day 23, as determined by assaying for $\alpha_4$ with monoclonal antibody B5G10, provided by Martin Hemler, Dana Farber Cancer Center, Boston, Mass. Further, in accordance with the present invention, it has been discovered that $\alpha_4$ and $\beta_3$ expression overlap between days 19–21, the window of implantation.

Figure 10:
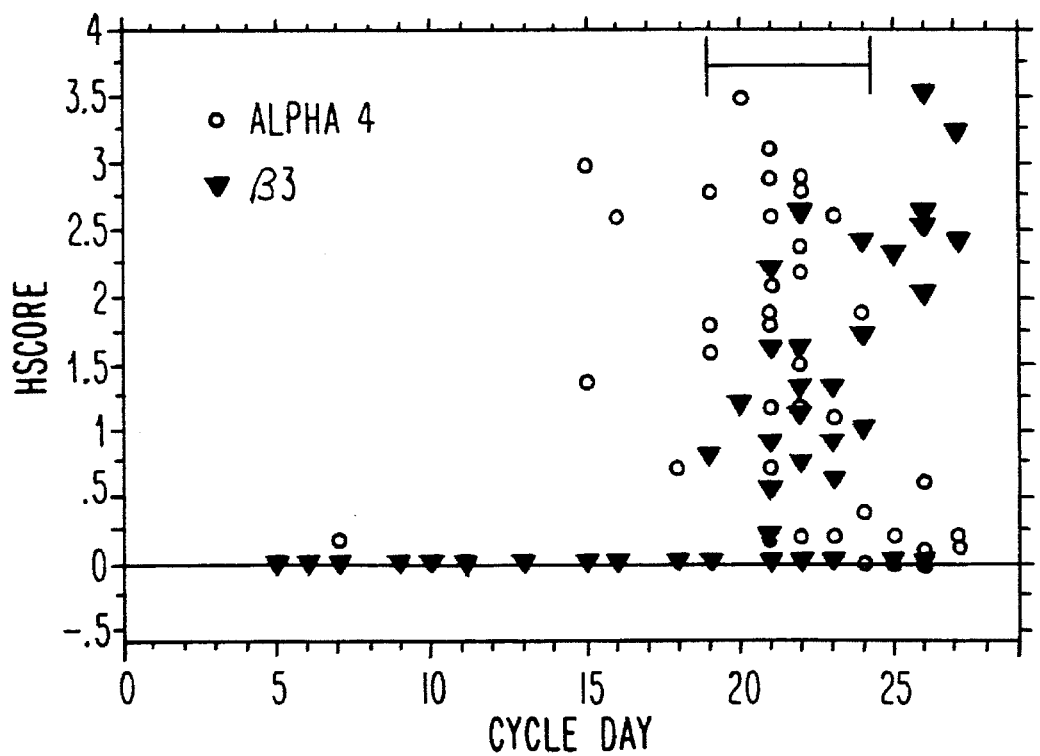
FIG. 10 displays the distribution of the $\alpha_4$ and $\beta_3$ integrin subunits during the normal menstrual cycle. Note the co-expression of both subunits corresponds to the putative window of implantation, postovulatory days 6–9.

As a result, as seen in FIG. 10, integrins define the window of implantation in the fertile, reproductive aged female. These cell adhesion molecules are dynamically regulated around the time of implantation and serve as excellent marker proteins for this time of the menstrual cycle. As shown in FIG. 10, the co-expression of $\alpha_4$ and $\beta_3$ (representing two different integrin species) coincide precisely with the known window of implantation (post ovulatory days 6–9, based on the work of Hertig et al., 1956 and Navot et al., 1992). In contrast to the $\beta_3$ integrin which appears to be disrupted in numerous females with infertility, the $\alpha_4$ integrin does not. While the process of implantation will likely involve many different proteins or factors, such as the co-expression of two different integrins as $\alpha_4$ and $\beta_3$, the loss of a single entity such as $\beta_3$ appears to be sufficient for the loss of fertility seen in these patients with endometriosis.

The present invention is directed to endometrium of the uterus of a mammal. The uterine wall is largely smooth muscle or myometrium. The endometrium, a glandular layer of variable thickness extremely sensitive to the hormones estrogen/progesterone, lines the myometrium. The endometrium is composed of several functional layers. The layer nearest the myometrium is termed the basalis layer, and the layer closer to the surface known as the functionalis. This tissue is made of epithelial cells, stromal (or mesenchymal) cells and endometrial leukocytes. The epithelial cells are either glandular (forming glands beneath the surface of the endometrium) or luminal (lining the surface of the endometrium). These different types of epithelium serve different purposes and staining patterns for different marker proteins are not always the same between glandular and luminal. It is the luminal surface that would encounter the human embryo first and is thought to be involved in initial attachment. The endometrium of premenopausal girls and postmenopausal women is atrophic due to the lack of the hormones, estrogen and progesterone. In the reproductive-aged woman, the endometrium undergoes cyclic developmental changes based on the ovarian cycle of hormone release. The first day of menstruation is the first day of the cycle; menstruation is generally completed by day 5. The endometrial growth then resumes under the influence of estrogen and progresses through the day 14, proliferative phase, and on to about day 28. From day 14 to day 28 the endometrium also shows signs of increased gland growth and secretion, secretory phase, due largely to the influence of progesterone. During the follicular phase, while follicles are growing in the ovary, and estrogen is the dominant hormone, the endometrium grows thicker. With ovulation (typically day 14 of a 28 day cycle) the women is exposed to estrogen plus progesterone. This is called the secretory or luteal phase, and is noted for a stereotypic series of histologic changes that proceeds as the cycle continues. These histologic changes are used by pathologists to date the endometrium, a process that remains controversial despite its use for the past 40 years. There have been no reliable immunohistochemical markers reported that have proven utility in dating the endometrium.

Luteal phase dysfunction (LPD) is a term for developmental delay of the endometrium. It is a known cause of infertility, because of dyssynchrony between the fertilized egg and the endometrium. If an embryo is ready to attach but the endometrium is delayed, then pregnancy is not likely to occur. The causes for LPD include inadequate hormonal output by the ovary, and may implicate defective signaling from higher centers such as inadequate gonadotropic hormone output from the pituitary or hypothalamus. LPD is a known cause of infertility and spontaneous abortion and can be corrected with hormone augmentation.

Embryo implantation stages include: apposition—when the epithelial cells of the embryo attach to the outer (luminal) epithelial cells of the maternal endometrial surface; adhesion; and invasion of trophoblast into the underlying stroma where it established itself and begins to grow. Contact with maternal blood vessels is made to gain nutrients and oxygenated blood and to rid itself of waste products during the invasion stage. The stage of development that the embryo reaches at the time of implantation is the blastocyst stage, which occurs at the same time as hatching. There is evidence that hatching is required before implantation occurs, perhaps because the embryo must have its epithelial cells exposed (out of the zona pellucida shell) to interact with the maternal cell layers. As set forth herein, this interaction occurs via integrins.

For purposes of the invention, endometriosis is defined as an ectopic occurrence of endometrial tissue, frequently forming cysts containing altered red blood cells. Stages of endometriosis have been established by the American Fertility Society, AFS. American Fertility Society: Revised American Fertility Society Classification of Endometriosis: 1985. Fertil Steril 1985; 43:351–352. The AFS defines stage I endometriosis as mild and stage II endometriosis as minimal.

As set forth in the present invention, infertility is defined as diminished or absent fertility such that a female mammal has adequate anatomical structures and equivocal function with possibility of pregnancy that may not proceed to term. Nulliparous includes, and is not limited to, endometrium from a female mammal who has not borne offspring. Nulliparous includes females who have conceived offspring and have not carried beyond 20 weeks gestation, instead having spontaneous abortions. Parous is defined in accordance with the present invention as having borne young, alive or dead, after a gestation of 20 weeks and a weight of 500 grams, for humans. Appropriate lengths of gestation and weight are applicable to other mammals such that they would be comparable to those set forth for humans.

For purposes of the current invention, mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans. Monoclonal antibodies useful in the practice of the invention include any monoclonal antibodies having an affinity to or binding to the $\beta_3$ subunit of integrin. An example of such a monoclonal antibody is SSA6. Monoclonal antibody SSA6 may be produced as described by Bennett et al., *PNAS* 1983, 80:2417 and Brass et al., *J. Biol. Chem.* 1985, 260:7876.

Monoclonal antibodies which recognize $\beta_3$ combined with another integrin subunit may also be used. One such monoclonal antibody is 23C6, which may be prepared according to the method of Davies et al., *J. Cell Biol.* 1989, 109:1817. Immunostaining with monoclonal antibodies such as 23C6 (specific to the intact $\alpha_v/\beta_3$ integrin, i.e. the vitronectin receptor) produces the identical pattern as SSA6 which only measures the $\beta_3$ subunit. This demonstrates that while $\alpha_v$ specific antibodies measure all the $\alpha v$ containing integrins, antibodies which recognize the intact $\alpha_v/\beta_3$ integrin or the $\beta_3$ subunit can be used to study this integrin (the $\alpha_v/\beta_3$ "vitronectin receptor").

Other monoclonal antibodies can be used. The preparation of monoclonal antibodies is known to those in the art. Particularly, the method of Kohler and Milstein, *Nature* 1975, 256:495 may be used to produce monoclonal antibodies for use in the invention.

Methods of obtaining endometrial tissue samples for analysis, include any surgical and nonsurgical technique known in the art. Surgical methods include, but are not limited to biopsy, dilation and curettage. Nonsurgical methods include, but are not limited to, uterine washings and uterine brushings with immunocytochemical evaluation.

Methods of detecting $\beta_3$ in the endometrium include all methods of identifying glycoproteins known in the art. These methods include, but are not limited to, immunohistochemistry techniques such as immunoblotting or Western blotting, immunoperoxidase staining, fluorescein labeling, diaminobenzadine and biotinylation.

Generally, immunohistochemistry involves staining cryosectioned tissue samples. As used herein, endometrium samples may be cryosectioned to about 4–8 μ thick. Endometrium is contacted with primary antibody, such as SSA6, followed by contact with secondary antibody, such as biotinylated goat anti-mouse antibody. Endometrium is then incubated in avidin-conjugated horseradish peroxidase macromolecular complex followed by chromagen incubation, such as diaminobenzadine. Fluorescein may then be added to observe integrin distribution.

Immunoblotting involves the analysis of protein, here integrin, on sodium dodecylsulfate-polyacrylamide gel electrophoresis SDS-PAGE. The gel is run under nonreducing conditions and the samples are transferred to a nitrocellulose membrane for example. The membrane is incubated in media containing primary antibody, such as SSA6. The filter is developed using a secondary antibody, such as alkaline phosphatase-conjugated goat anti-mouse antibody.

The methods of the present invention directed to predicting endometriosis comprise obtaining a sample of endometrium, identifying the sample of endometrium as nulliparous, contacting the sample with a monoclonal antibody specific for $\beta_3$ integrin, assaying for $\beta_3$ integrin in the sample, and correlating the absence of $\beta_3$ integrin with endometriosis, wherein endometriosis is mild/minimal endometriosis.

Methods of using monoclonal antibodies to $\beta_3$ integrin to predict endometriosis are also within the scope of the invention and comprise obtaining a sample of endometrium, identifying the sample of endometrium as nulliparous, contacting the sample with a monoclonal antibody specific for $\beta_3$ integrin, assaying for $\beta_3$ integrin in the sample, correlating the absence of $\beta_3$ integrin with endometriosis, wherein the endometrium is identified as mild/minimal endometriosis.

The methods of diagnosing infertility and for detecting the window for embryo implantation in the endometrium of a mammal are also within the scope of the invention. As provided herein, the $\beta_3$ subunit of integrin appears at day 20 of the menstrual cycle. It is also provided herein that $\alpha_v/\beta_3$ on endometrial epithelium binds fibronectin, vitronectin and osteopontin. These molecules may provide a bridge between the $\alpha_v/\beta_3$ integrin of the endometrium and the embryo. Further, patients with luteal phase dysfunction have delayed endometrial maturation, infertility and negative staining for $\beta_3$ on days 20 through 24. Thus, the optimal time for fertility may be determined by repetitively testing endometrial samples at a plurality of stages in the menstrual cycle. As such, screening for $\beta_3$ provides a method of diagnosing infertility and for detecting the window of embryo implantation in the endometrium. The window of implantation is that time when the endometrium of the uterus is available for embryo implantation. This window is preferably from day 19 to day 23, and more preferably day 20 of the human menstrual cycle, marked by the expression of $\alpha_v/\beta_3$ integrin.

Similar cycles are known for other mammals—it is within the ordinary skill in the art to adopt the foregoing methodology to such cycles.

The present invention is also directed to methods of in vitro fertilization. Once the $\beta_3$ subunit of integrin is detected in an animal selected for pregnancy, a fertilizable egg (or eggs) from the same or different animal could be replaced into the uterus to establish pregnancy. The egg and appropriate sperm are combined to produce a zygote in vitro. For purposes of the invention, in vitro fertilization may take place in a petri dish, in a test tube or the like. In addition, in vitro fertilization may also refer to independently adding eggs and sperm to the fallopian tubes such that the zygote is formed therein. In any event, the zygote is introduced to the uterus of the animal selected for pregnancy and monitored for implantation into the endometrium of the uterine wall.

Alternatively, the invention is directed to methods of preventing embryo implantation. Such may be carried out by contacting the endometrium with a neutralizing Fab fragment specific for $\beta_3$. For purposes of the present invention, Fab fragments from monoclonal antibodies which bind $\beta_3$ are within the scope of the invention. Fab fragments include, but are not limited to, Fab fragments from monoclonal antibodies SSA6 and 23C6. The Fab fragment may remain in vivo for a therapeutically effective time to prevent embryo implantation. The Fab fragment comprises the ligand binding portion of a monoclonal antibody for $\beta_3$, i.e. the binding site for $\beta_3$. A neutralized Fab fragment is used in place of a typical monoclonal antibody to reduce the possibility of an inflammatory reaction.

Contraception is a further embodiment of the invention. A contraceptive may include a therapeutically effective amount of neutralizing Fab fragment monoclonal antibodies specific for $\beta_3$ integrin in a pharmaceutically acceptable carrier, preferably adapted for intrauterine application. The Fab fragment may be from a monoclonal antibody which recognizes $\beta_3$, such as and not limited to SSA6. The contraceptive may include $\beta_3$ in combination with other integrin subunits, such as and not limited to $\alpha_v$ for example. In the case of $\alpha_v\beta_3$, the Fab may be from monoclonal antibody 23C6.

Compounds which specifically block binding of the embryo to this $\alpha_v/\beta_3$ receptor are also included within the scope of the present invention. Examples include peptides containing the amino acid sequence arginine-glycine-aspartic acid, RGD (Pierschbacher et al., "Synthetic Peptide with Cell Attachment Activity of Fibronectin", PNAS 1983, 80:1224) which is the active binding site for the vitronectin receptor. This sequence has been reported to block attachment of pregnancy derived cells (trophoblast) in vitro by researchers, Kao et al., "The Human Villous Cytotrophoblast: Interactions with Extracellular Matrix Proteins, Endocrine Function, and Cytoplasmic Differentiation in the Absence of Syncytium Formation", *Development* 1988, 130:693. Thus, a contraceptive containing the sequence RGD may be administered locally to prevent embryo implantation.

Pharmaceutically acceptable carriers include, and are not limited to, vaginal suppositories, intrauterine devices (IUD), gels such as slow release formulation, for example, depo forms of hormones—microcrystals injected and slowly released into the systemic circulation or delivered in silastic tubing. Contraceptive formulations would be administered in about 10 µg/ml.

Methods of monitoring endometrial maturation is also within the scope of the present invention. The endometrium may be monitored for embryo receptivity, embryo implantation, infertility, endometrial replenishment and ovulation.

Diagnostic kits are also within the scope of this invention. Such kits include monoclonal antibodies to rapidly detect $\beta_3$ in solution; an absorbant detection device which contains pre-absorbed antibody against $\beta_3$ and to which uterine washings can be applied; a developer to make $\beta_3$ visible when present.

Compounds which prevent $\beta_3$ expression are also included within scope of present invention. Although the regulatory signal for the induction of the endometrial integrin on day 19 to 20 is not yet secured, as a result of the present invention, peritoneal fluid is now known to contain bioactive agents which appear to be related to defective integrin expression in women with infertility and endometriosis. Bioactive components with an abnormal peritoneal milieu may lead to a breakdown in the paracrine crosstalk between endometrial cells within the uterus. Candidates include interleukin-1β receptor antagonist, elevated in women with minimal and mild endometriosis and recently demonstrated to interfere with implantation in a rodent model, Simon, C., et al., Annual Meeting of the American Fertility Society, Montreal, S2-Abst O-3, 1993. Open or unobstructed fallopian tube may be a prerequisite to endometriosis-mediated effects of endometrial $\beta_3$ integrin.

In accordance with the present invention, the hydrosalphinx fluid is herein identified as a potential candidate for causing endometrial defects. The methods of the present invention determined that over 50% of women with distal occlusion of the fallopian tube, which causes tubal fluid accumulation, were found to have a loss of the $\alpha_v\beta_3$ integrin during the time of implantation. Three women who were $\beta_3$ negative had complete correction of the defect of integrin expression. These three women underwent endometrial biopsy before and after the hydrosalphinx was surgically removed. This suggests that fluid from the tube, which accumulates and is allowed to empty back into the uterus causes a dysfunction in the endometrium, resulting in infertility. This is consistent with recent reports showing a decrease in uterine receptivity in women with hydrosalphinx compared to women without hydrosalphinx entering an IVF-in vitro fertilization clinic.

The present invention is directed to a method of treating a mammal having endometriosis comprising screening a mammal suspected of having endometriosis for the presence of hydrosalphinx fluid and inactivating said fluid. The step of inactivating the hydrosalphinx fluid includes, and is not limited to, removing the fluid or contacting antibodies to the fluid. Antibodies may include monoclonal, polyclonal, chimeric antibodies and Fab fragments. Alternatively, screening for factors which may be isolated from hydrosalphinx fluid and inactivating said factor is contemplated by the present invention.

The present is also directed to preventing embryo implantation by contacting fallopian tubes or the uterus with hydrosalphinx fluid or hydrosalphinx fluid factors. Hydrosalphinx may remain in vivo for a therapeutically effective time to prevent embryo implantation.

Contraception is a further embodiment of the invention. A contraceptive may include a therapeutically effective amount of hydrosalphinx fluid, or factors isolated therefrom. A contraceptive may alternatively be introduced together with a pharmaceutically acceptable carrier. The dosage of a contraceptive of the present invention is determined with regard to weight, and clinical condition of the patient. The proportional ratio of active ingredient to carrier will naturally depend on the chemical nature, solubility, and stability of the compounds, as well as the dosage contemplated. Contraceptives of the present invention are preferably adapted for fallopian tube or intrauterine application.

The present invention is further described in the following examples. These examples are not to be construed as limiting the scope of the appended claims.

EXAMPLES

Human Samples

Endometrium was obtained from 35 reproductive age women at the time of hysterectomy. Tissue was obtained from the early proliferative (day 5) through late secretory phase (day 28) and all hysterectomies were performed for benign disease. Endometrial biopsies were performed on women as part of their evaluation for infertility. All patients were cycling normally and none had received hormones for at least 3 months prior to surgery. Dating of the endometrium was assessed according to the criteria of Noyes et al., "Dating the Endometrium", *Fertil. Steril.* 1950, 1:3. Endometrial biopsies were evaluated in the context of timing of ovulation and/or the onset of the next menstrual period. Samples were judged as "out of phase" if histologic dating was delayed by 3 or more days relative to the predicted day of the menstrual cycle. Proliferative endometrium was categorized based on histology and on last menstrual period. Samples were transported on ice to the laboratory and were snap frozen on dry ice and stored at −70° C.

Antibodies

Monoclonal antibodies (Mabs) P1H5, P1B5, P1D6 specific to $\alpha_2$, $\beta_3$, $\alpha_5$ subunits, respectively, were acquired from Drs. Elizabeth Wayner and William Carter. Mabs TS2/7 and B-5H10 directed against the $\alpha_1$ and $\alpha_4$ subunits, respectively were acquired from Dr. Martin Hemler. GoH3, a specific Mab directed against $\alpha_6$ was acquired from Dr. Arnoud Sonnenberg. Mab SSA6 specific to the $\beta_3$ subunit was acquired from Drs. Joel Bennett and James Hoxie. Mab LM142 against $\alpha_v$ was acquired from Dr. David Cheresh. The $\beta_4$ antibody was acquired from Dr. Steven Kennel. The 23C6 antibody which recognizes $\beta_3$ attached to $\alpha_v$ was obtained from Michael Horton.

Immunohistochemistry

Immunoperoxidase staining was performed on cryostat sections of endometrium samples from throughout the menstrual cycle. Serial cryosections 4–8 μ thick were placed onto poly-L lysine coated slides, fixed in –20° C. acetone for 10 minutes, and stained using Vectastain Elite® ABC kits (Vector Laboratories, Burlingame, Calif.). Diaminobenzadine (DAB; Sigma Chemical Co., St. Louis, Mo.) was used as the chromagen. Primary antibody was placed on cryosections following blocking with 1% bovine serum albumin in PBS, and allowed to bind at room temperature for 1 hour. A phosphate buffered saline (PBS) pH 7.2 to 7.4 rinse was followed by secondary antibody consisting of biotinylated goat anti-mouse antibody for 30 minutes. Following a PBS rinse, the endogenous peroxidases were quenched with a 30 minute incubation with 0.3% $H_2O_2$ in absolute ethanol, followed by a 30 minute rehydration in PBS. Avidin:biotinylated horseradish peroxidase macromolecular complex (ABC) was then incubated on the sections for 30 minutes before adding diaminobenzadine for 3 minutes to complete the reaction. Some samples were treated with 1:200 dilution of fluorescein-labeled anti-mouse antibodies for 1 hr., for immunofluorescent microscopy. Samples were subsequently washed in PBS and mounted. The resulting staining was evaluated on a Nikon microscope at low (100x) and higher (400X) magnification with or without fluorescence. Staining was judged as absent (–), weak (±), moderate (+) or strong (++). Examples of each is presented in FIGS. 3A–3D. Photomicrographs were made using Kodak T-MAX 100 ASA film.

Integrin Distribution in Normal Endothelium

The distribution of $\alpha_2$, $\alpha_3$, $\alpha_6$, and $\beta_4$ subunits of integrins which recognize primarily collagen (Col) and/or laminin (LM) is shown in FIGS. 1A–D. These subunits were present on glandular epithelium (←) throughout the menstrual cycle. Their distribution within the endometrium was typical of that seen for most epithelial tissues. The $\alpha_2$ and $\beta_3$ subunits were distributed around the entire circumference of the cells, while the $\alpha_6$ and $\beta_4$ subunits appeared to be localized at the basolateral surface, adjacent to the basement membrane (BM) of the endometrial glands. The expression of these subunits by the mesenchyme (*) was less pronounced. While moderate staining was seen for $\alpha_6$ on stromal cells (FIG. 1C) very little staining was noted for $\beta_4$. The expression of the $\alpha_4$ and $\alpha_5$ subunits of integrins known to bind fibronectin (Table 1) was quite restricted. The $\alpha_4$ subunit was undetectable above background staining (compare FIG. 1E with FIG. 2C) in either epithelium or mesenchyme. The $\alpha_5$ subunit (FIG. 1F), representative of the classic fibronectin receptor was not seen on the epithelial components, but was strongly expressed in the mesenchyme which is rich in fibronectin.

TABLE 1

DISTRIBUTION OF INTEGRINS BY LIGAND SPECIFICITY

| | Ligands | |
|---|---|---|
| | Collagen/Laminin | Fibronectin/Vitronectin |
| Integrin Subunit | $\alpha_1/\beta_1$ | $\alpha_4/\beta_1$ |
| | $\alpha_2/\beta_1$ | $\alpha_5/\beta_1$ |
| | $\alpha_3/\beta_1$ | $\alpha_v/\beta_1$ |
| | $\alpha_6/\beta_1$ | $\alpha_v/\beta_3$ |
| | $\alpha_6/\beta_4$ | |

Figure 2B:
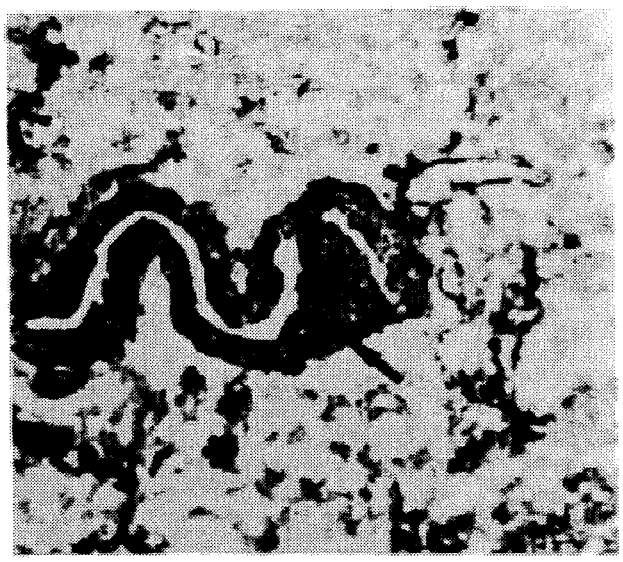
Figure 2C:
Figure 3A:
FIGS. 3A–3D exhibit immunostaining of $\alpha_v$ and $\beta_3$ (the two pairing subunits of the vitronectin receptor integrin) in proliferative phase vs. secretory phase endometrium. The staining intensity of $\alpha_v$ in the proliferative phase (A) was judged as "+" for the stromal cells (*) and "±" for glandular $\alpha_v$ (←). Immunostaining for $\alpha_v$ in day 22 endometrium (B) demonstrates a significant increase in glandular staining (example of "++" staining intensity). Likewise, the staining for $\beta_3$ was absent in proliferative epithelium (C; ←) and was notably increased in this day 22 secretory endometrium (D). Magnification: 125X.
Figure 3B:
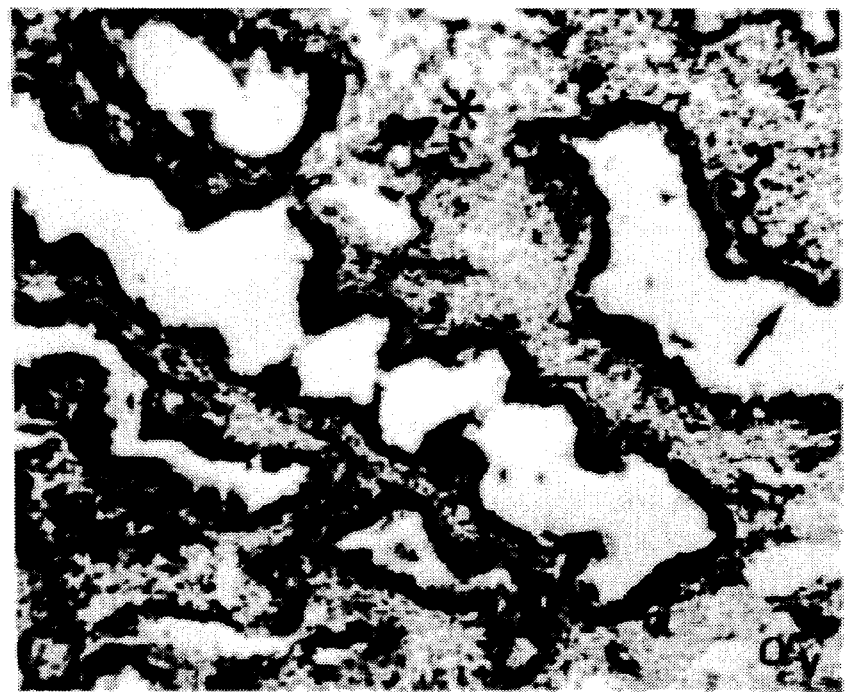
Figure 3C:
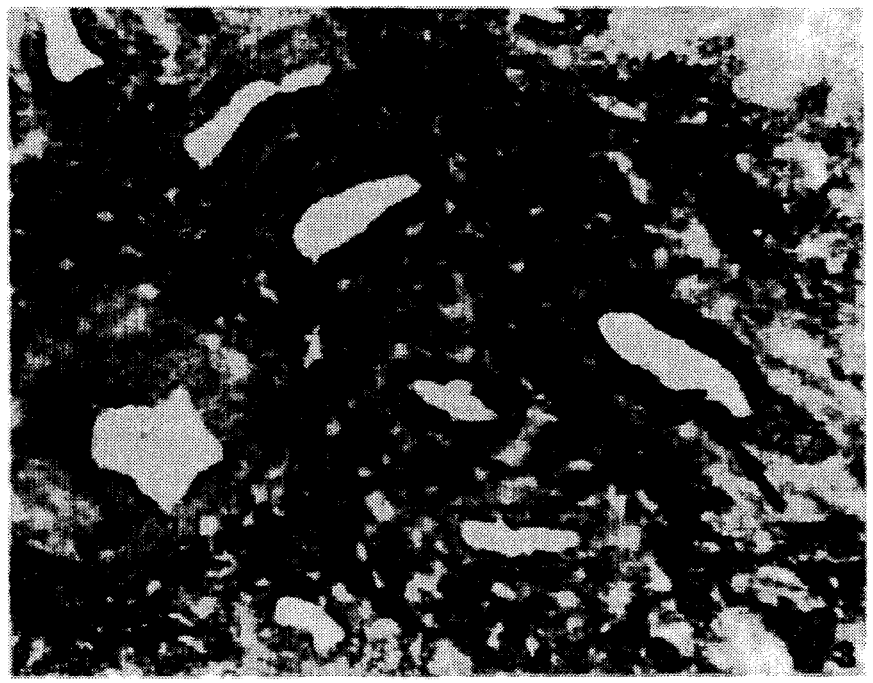
Figure 3D:
Figure 4A:
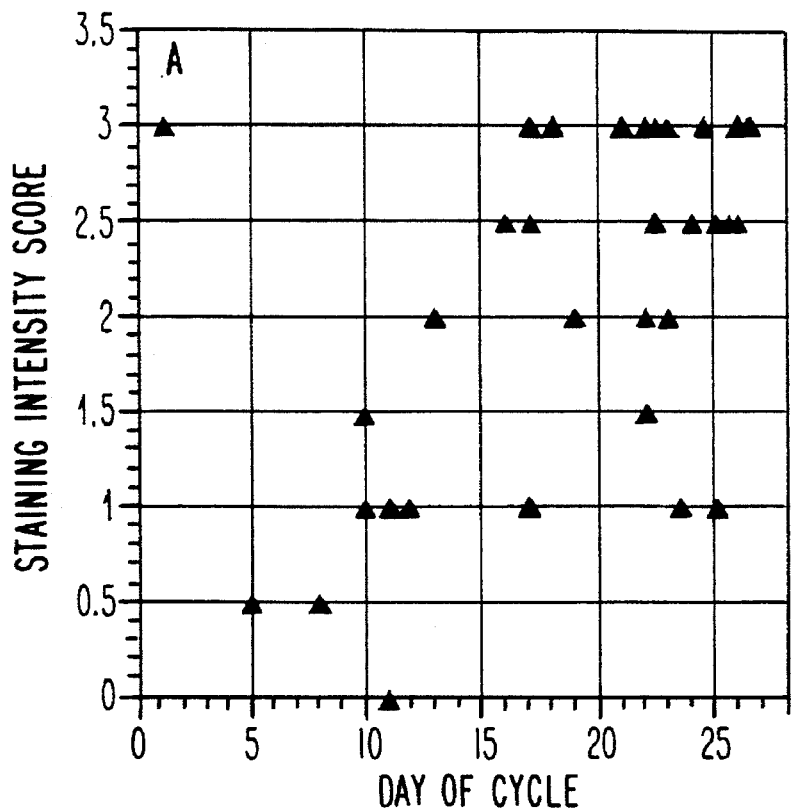
FIGS. 4A and 4B show relative intensity of staining for the epithelial $\alpha_v$ and $\beta_3$ subunits in 35 endometrial samples throughout the menstrual cycle. The pattern of expression for $\alpha_v$ is shown in A, shows a gradual increase in staining throughout the menstrual cycle. In contrast, the pattern for $\beta_3$ in B, shows a more abrupt rise in this integrin subunit around day 20 of the menstrual cycle. Samples were staged according to the last menstrual cycle. Sections were assigned a score of 0 (−; negative), 1 (±; weak), 2 (+; moderate) or 3 (++; strong), by a blinded observer, and confirmed by a second observer.
Figure 4B:
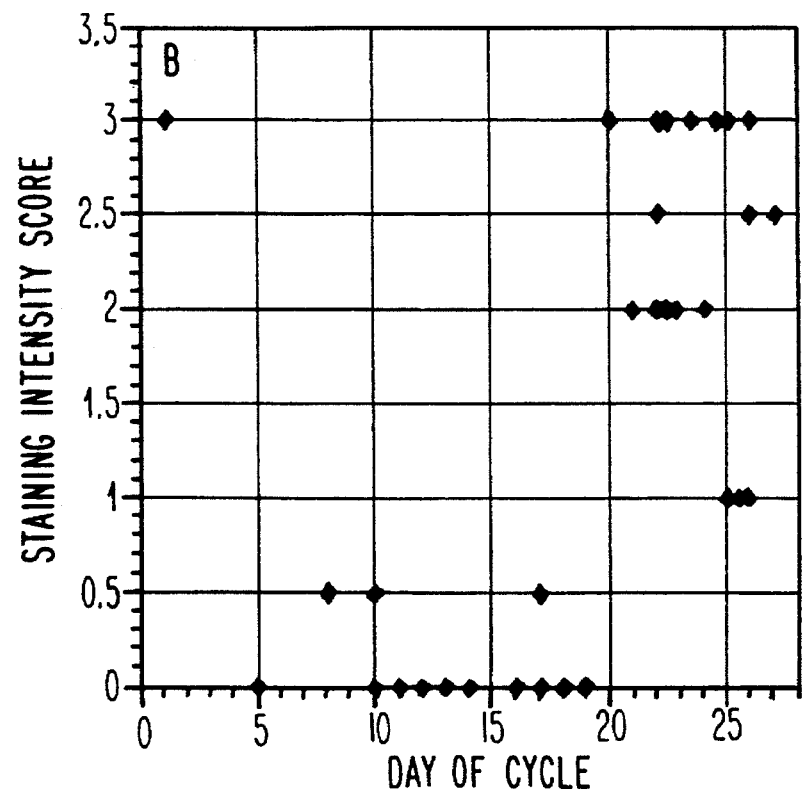

The intensity of immunostaining for three other subunits of integrins was found to change in a menstrual cycle-dependent manner. Immunostaining for $\alpha_1$ in the proliferative phase (FIG. 2A) was only slightly above background levels (FIG. 2C). The intensity of staining increased throughout the secretory phase (FIG. 2B). This intense circumferential staining was found on glandular and luminal epithelium on all samples from day 15 to 28. Likewise, $\alpha_v$ was weakly expressed on both the epithelium and mesenchyme in the proliferative phase (FIG. 3A) and staining increased gradually during the secretory phase to the level noted in FIG. 3B. During the proliferative phase $\beta_3$ staining was only present on the mesenchymal cells (FIG. 3C). Increased $\beta_3$ staining was apparent on the endometrial epithelium only after day 19 of the menstrual cycle (FIG. 3D) on the luminal as well as glandular epithelium, and was also present in a pericellular distribution. In contrast, the basalis layer did not significantly stain for either $\alpha_v$ or $\beta_3$. This changing pattern of epithelial $\alpha_v$ and $\beta_3$ throughout the cycle was studied in 35 endometrial samples and is depicted graphically in FIGS. 4A and 4B.

Collagen/laminin receptors (col/LM) characterized by $\alpha_2$, $\alpha_3$ and $\alpha_6$ were uniformly expressed throughout the menstrual cycle, see Table 2. The pericellular distribution of $\alpha_2$ and $\alpha_3$ subunits was distinctly different from that of $\alpha_6$ subunit. Characteristic of a laminin receptor, $\alpha_6$ was concentrated on the basolateral surface. The $\beta_4$ subunit which pairs with $\alpha_6$, was also found distributed on the basolateral surface of epithelial cells, and its distribution appeared even more restricted to the basal pole. The $\alpha_5/\beta_1$ integrin, a major fibronectin receptor, was also uniformly expressed throughout the menstrual cycle. Unlike the collagen and laminin receptors, the distribution of $\alpha_5/\beta_1$ was limited to the mesenchyme.

The temporal pattern of distribution of $\alpha_v$ was varied. Immunostaining was first detected prior to the secretory phase with an increase in intensity throughout the cycle. One subunit known to pair with $\alpha_v$ is $\beta_3$. $\beta_3$ is not characteristically present on epithelial cells. The abrupt appearance of the $\beta_3$ subunit after day 19 suggests that expression of the vitronectin receptor is regulated in human endometrium. The increased epithelial $\alpha_v/\beta_3$ staining in normal cycles correlates to an implantation window within the secretory phase. While the physiologic basis for the implantation window has not been previously established, a proposed role of integrins in the initial interaction between maternal and embryonic cells indicates an endometrial period of receptivity.

TABLE 2

DISTRIBUTION OF INTEGRIN SUBUNITS IN
NORMAL ENDOMETRIUM DURING THE
MENSTRUAL CYCLE

Figure 5A:
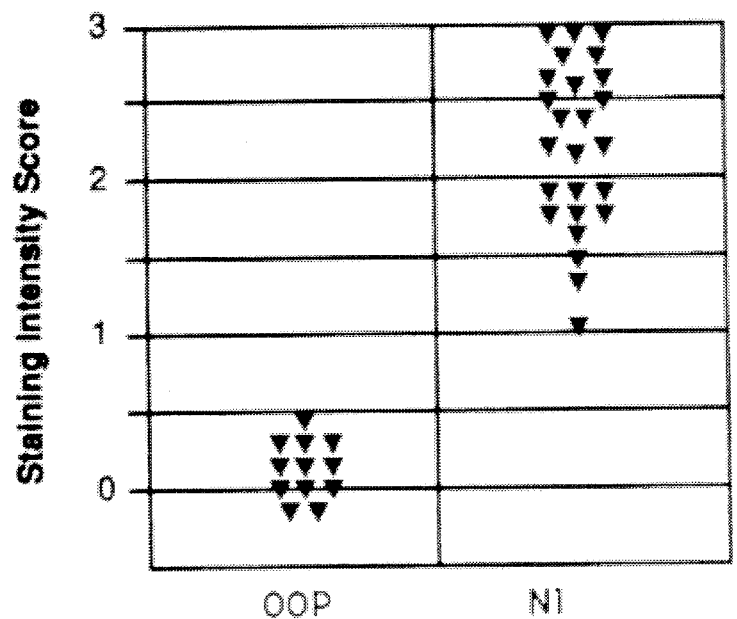
FIGS. 5A–5C depict staining intensity of epithelial $\beta_3$ in 12 infertility patients with delayed endometrial maturation. Endometrium was collected from women undergoing evaluation for infertility. The biopsies were separated into two groups based on the correlation between histologic criteria and the menstrual cycle dating based on the time of ovulation and/or the subsequent menstrual period. Patients with endometrial biopsies 3 or more days "out of phase" (OOP group) were compared with 25 endometrial biopsies that were "in phase" (Normal) and shown in A. Sections were assigned a score of 0 (−; negative), 1 (±; weak), 2 (+; moderate) or 3 (++; strong), based on the intensity of epithelial $\beta_3$ staining. Examples of immunohistochemical staining of an "out of phase" biopsy (B) and a normal "in phase" sample (C) is included to contrast the epithelial $\beta_3$ staining in each group. Magnification: 400X.
Figure 5B:
Figure 5C:

| Cell Type | Col/LM | | | | | FN/VN | | | |
|---|---|---|---|---|---|---|---|---|---|
|  | $\alpha_1$ | $\alpha_2$ | $\alpha_3$ | $\alpha_6$ | $\beta_4$ | $\alpha_4$ | $\alpha_5$ | $\alpha_v$ | $\beta_3$ |
| Epithelial |  |  |  |  |  |  |  |  |  |
| proliferative | o | ● | ● | ●b | ●b | o | o | o | o |
| early secretory | ● | ● | ● | ● | ● | o | o | * | o |
| late secretory | ● | ● | ● | ● | ● | o | o | ● | ● |
| Stromal |  |  |  |  |  |  |  |  |  |
| proliferative | o | o | o | ● | o | o | ● | ● | ● |
| early secretory | o | o | o | * | o | o | * | ● | ● |
| late secretory | * | o | o | ● | o | o | * | ● | ● | b = basolateral distribution of staining
● = + or ++ staining
* = ± staining
o = − staining Integrins in Discordant Endometrium The presence of the epithelial $\beta_3$ subunit appeared to be a consistent internal marker of luteal phase maturation, and the timing of $\beta_3$ expression correlated with the peri-implantation period or window of embryo implantation. To investigate whether this phenomenon would be useful in the clinical evaluation of endometrial biopsies, immunostaining was performed on luteal phase endometrial samples from cycles which showed evidence of maturational delay. Endometrial biopsies from 25 women who had concordance of menstrual and histologic dating ("Normal" group) were compared to 12 biopsies which were identified as ≧3 days out of phase (OOP) based on either the time of ovulatory or the subsequent menses. Samples were immunostained for $\alpha_1$, $\alpha_v$ and $\beta_3$ subunits. All biopsies were performed on days 20 to 24 of the menstrual cycle. In all instances, immunostaining for these three antigens was present on endometrial epithelia from the normal group. In biopsies which were delayed by 3 days or more, $\alpha_1$ and $\alpha_v$ staining was present, but epithelial $\beta_3$ staining was absent. The comparison of $\beta_3$ staining intensity in the two groups is shown in FIG. 5A. Accompanying photomicrographs of $\beta_3$ immunostaining from out of phase biopsies (OOP; B) and normal "in phase" biopsies (C) is included, which demonstrates the discrepancy seen in $\beta_3$ staining. In subsequent treatment cycles, 2 OOP patients underwent repeat biopsy during a normalized cycle at which time immunostaining for epithelial $\beta_3$ was present. This suggests that the lack of $\beta_3$ was not an intrinsic defect in the OOP group. Rather, the discordant biopsies which lacked $\beta_3$ had not yet established the mid-luteal phenotype of normal day 20 to 24 endometrium.

Cell Harvest and NP-40 Extraction

To further demonstrate that immunohistochemical staining accurately reflected changes in the expression of $\beta_3$ subunit on endometrial epithelium, immunoblots (Western blots) were performed on samples of enriched endometrial glandular elements from proliferative and secretory phase. Four samples of endometrium were obtained for the evaluation of the $\beta_3$ subunit in proliferative (n=2) and late secretory (n=2) endometrial epithelium. Each sample was placed in Dulbecco's modified Eagle's medium (DMEM; Sigma, St. Louis, Mo.), supplemented with 10% fetal bovine serum (Flow Laboratories, McLean, Va.) glucose (4500 mg/L), Hepes buffer (25 mM), L-glutamine (584 mg/L), and sodium bicarbonate (3.7 gms/L). Endometrium was minced in a plastic petri dish prior to incubation with 6 mg of collagenase (type 1A, 550 units/mg; Sigma, St Louis, Mo.) for 2 hours at 37° C. utilizing modifications of the procedures described by Satyaswaroop et al. in "Isolation and Culture of Human Endometrial Glands", J. Clin. Endocr. Metab. 1979, 48:639. The resulting suspension was successively passed through a 250 μm sieve and a 38 μm sieve (Newark Wire Cloth Co, Newark N.J.). The course (250 μm) sieve removed undigested material, while the second retained the glandular elements and excluded the individual stromal and blood cells. After thorough rinsing, the glandular elements were obtained by backwashing with 10 to 20 ml of DMEM. The isolated glandular structures were then transferred to a 1.5 ml microfuge tube and centrifuged 3 times (82×g) for 2 minutes with intermittent washes with PBS. Membrane extracts were prepared by adding small volumes (100–200 μl) of 10 mM Tris-acetate, pH 8.0, 0.5% NP-40, 0.5 mM $Ca^{2+}$ (TNC) with 2 mM PMSF (phenyl methyl-sulfonyl fluoride) to the final pellet, pipetted and incubated on ice for 15 minutes. The lysate was centrifuged for 5 minutes at 16,000×g in a microcentrifuge. The resulting supernatant was called NP-40 extract and was frozen at −70° C. until use. A portion of the original, undigested tissue was cryosectioned for immunohistochemical localization of $\beta_3$.

Gel Electrophoresis and Immunoblots

The protein concentration of each NP-40 extract and an extract of platelets (positive control) was determined using technique described by Lowry et al., "Protein Measurement with Folin Phenol Reagent", J. Biol. Chem. 1951, 193:265. Samples with equal amounts of protein were added to electrophoresis sample buffer (62.5 mM Tris base, 2% SDS, 10% glycerol, pH 6.8). Samples were analyzed by SDS-PAGE using 6% polyacrylamide gels, using non-reducing conditions described by Laemmli, U. K., "Cleavage of Structural Proteins During Assembly of the Head of Bacteriophage T4", Nature 1970, 227:680. The gel was transferred to nitrocellulose using a Biorad transfer apparatus (Biorad, Richmond, Calif.) and blocked with 4% BSA in PBS with 0.2% Na Azide for 1 hour. After addition of primary antibody (SSA6 supernatant) for 2 hours, the gels were developed using an alkaline phosphatase-conjugated secondary antibody (Promega Corp., Madison, Wis.) according to methods described by Albelda et al., "EndoCAM:A Novel Endothelial Cell-Cell Adhesion Molecule", J. Cell Biol. 1990, 110:1227.

Figure 6C:
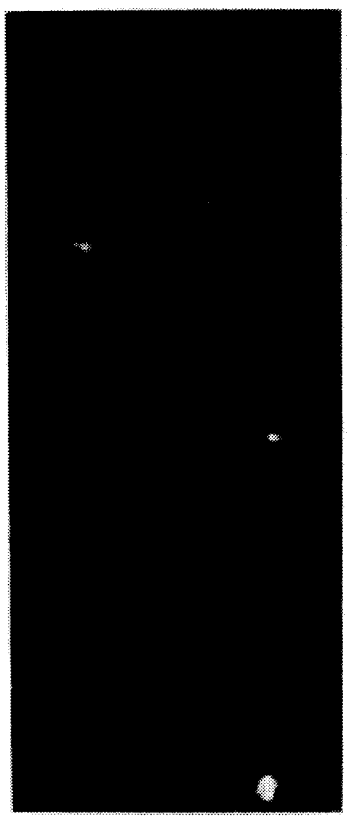
FIGS. 6A–6D exhibit immunoblot analysis of proliferative and secretory endometrium, stained for the $\beta_3$ subunit. (A) Immunoblot of platelet extract (lane 1) compared with 2 samples from the early and mid proliferative phase (lanes 2,3) and from the luteal phase (lane 4 and 5; days 23 and 26, respectively) demonstrates a band at approximately 95 kD molecular weight, corresponding to $\beta_3$. Samples of endometrium were partially digested with collagenase and the glandular elements obtained (B) using a modification of the methods of Satyaswaroop et al., "Isolation and Culture of Human Endometrial Glands", *J. Clin. Endocr. Metab.* 1979, 48:639. The glands appear as hollow structures free from surrounding stroma. Immunofluorescence of samples from lanes 3 and 4 (C and D, respectively) corresponds to the absence or presence of the 95 kD band in A. Magnification: 400X.
Figure 6D:
Figure 6A:
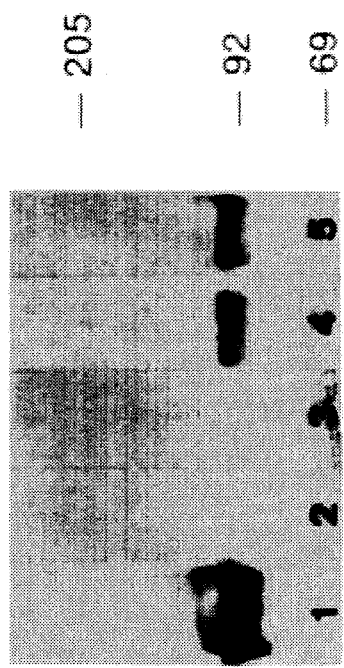
Figure 6B:
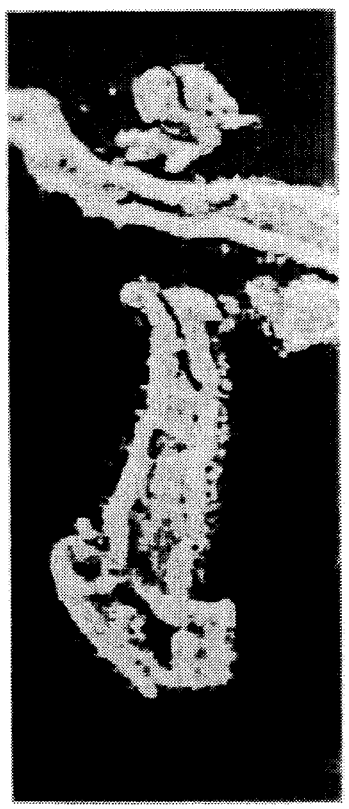

As shown in FIG. 6A, proliferative phase epithelial structures had little to no immunostaining at 95 kD (lanes 2 and 3), compared to the positive control (platelet extract; lane 1) or to samples from the secretory phase (lanes 4 and 5) which showed strong staining for $\beta_3$. The isolated endometrial glands appeared as tubular structures free of surrounding stroma (FIG. 6B). Immunofluorescent staining for $\beta_3$ from samples corresponding to lanes 3 and 4 (mid proliferative phase and day 23, respectively) are shown in FIGS. 6C and D. Note the absence of glandular staining in the proliferative sample, while both glandular and luminal immunostaining is obvious from the secretory phase. These data confirm that the expression of epithelial $\beta_3$ in human endometrium is a cycle specific phenomenon.

Determination of Endometriosis Patient Selection

Biopsies were obtained from throughout the menstrual cycle from 500 women undergoing evaluation for infertility at the University of Pennsylvania. The biopsies were screened for participation in the study based on criteria including accurate knowledge of menstrual cycle day or "in phase" histology and freedom from menstrual cycle disturbances (anovulation (suspension or cessation of ovulation), perimenopausal state (dysfunctional uterine bleeding), luteal phase defect (histologic evidence of maturational delay of the endometrium), the presence or use of an intrauterine device or endometritis (inflammation of endometrium due to infectious agents or chemical irritation). Patients with endometrial hyperplasia (an increase in the number of cells in endometrium), neoplasia (a pathologic process resulting in formation or growth of abnormal tissue or tumors, benign or malignant), and those on hormonal therapy (including oral contraceptives, estrogen replacement therapy and progestens) were likewise excluded. Two hundred and sixty eight women were eligible for enrollment in this study, ranging from cycle day 2 through 27. The most common primary diagnosis was endometriosis (41.4%) followed by unexplained infertility (23.5%), see Table 3. Due to the participation criterion of normal "in phase" histology as set forth above, all cases of luteal phase deficiency were excluded.

TABLE 3

Diagnoses of Subjects with Infertility Undergoing Endometrial Biopsy (N = 268)

| Diagnosis | Number (%) |
| --- | --- |
| endometriosis | 111 (41.4) |
| tubal disease | 38 (14.2) |
| pelvic adhesions | 17 (6.3) |
| male factor | 18 (6.7) |
| fibroids | 9 (3.4) |
| habitual pregnancy loss | 6 (2.2) |
| in utero DES exposure | 4 (1.5) |
| hyperprolactinemia | 2 (0.7) |
| unexplained infertility | 63 (23.5) |

Endometrial biopsies of 241 patients were obtained after day 19 (post ovulatory day 6 or greater) based on urinary luteinizing hormone, LH, surge or next menstrual period, a time in the menstrual cycle when epithelial $\beta_3$ is expressed, Lessey, et al., supra. The remaining patients (n=27) were biopsied prior to day 20 and therefore would not be expected to produce the $\beta_3$ integrin. Based on routine infertility workup, including diagnostic laparoscopy which involves the examination of the contents of peritoneum with a laparoscope passed through the abdominal wall, 105 (43.6% of the group) of these women had endometriosis. The 105 women were then considered as the test cases. Twenty women with endometriosis also had documented prior fertility, previously produced young, having parity $\geq 1$, where each women had $\geq 1$ prior birth, and had undergone bilateral tubal ligation or had clearly identified male factor infertility, (or infertility of the male partner). These were chosen to serve as fertile controls. The remaining 116 women (48.1% of the group) were considered the infertile controls.

Immunohistochemistry

Immunoperoxidase staining was performed on the 241 samples as described by Lessey, et al., supra. Briefly, immunoperoxidase staining was performed on cryostat sections of endometrium throughout the menstrual cycle. Serial cryosections 4–8 μ thick were placed onto poly-L lysine coated slides, fixed in −20° C. acetone for 10 minutes, and stained using Vectastain Elite® ABC kits (Vector Laboratories, Burlingame, Calif.). Diaminobenzadine (DAB; Sigma Chemical Co., St. Louis, Mo.) was used as the chromogen. Primary antibody consisting of SSA6 (specific to the $\beta_3$ subunit of the vitronectin receptor) was placed on cryosections following blocking with 1% bovine serum albumin in phosphate buffered saline, PBS, and allowed to bind at room temperature for 1 hour. A PBS rinse, pH 7.2 to 7.4, was followed by secondary antibody consisting of biotinylated goat anti-mouse antibody for 30 minutes. Following PBS rinse, the endogenous peroxidases were quenched with a 30 minute incubation with 0.3% $H_2O_2$ in absolute ethanol, followed by a 30 minute rehydration in PBS. Avidin: biotinylated horseradish peroxidase macromolecular complex (ABC) was then incubated on the sections for 30 minutes before adding diaminobenzadine for 3 minutes to complete the reaction. Samples were subsequently washed in PBS and mounted.

Figure 7:
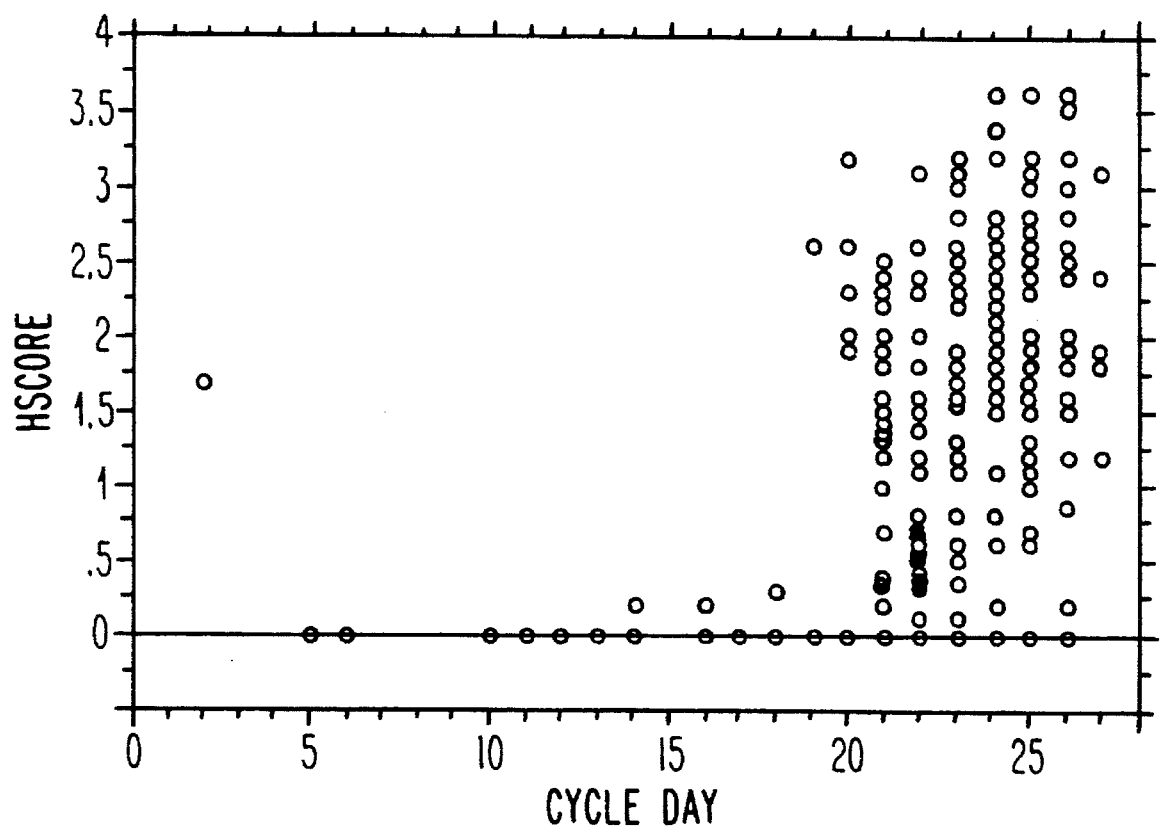
FIG. 7 is a scattergram showing the immunohistochemical staining for the $\beta_3$ integrin subunit in endometrial samples form day 1 to 28 of the cycle. All samples had known endometrial dating, and none were out of phase, histologically.
Figure 8A:
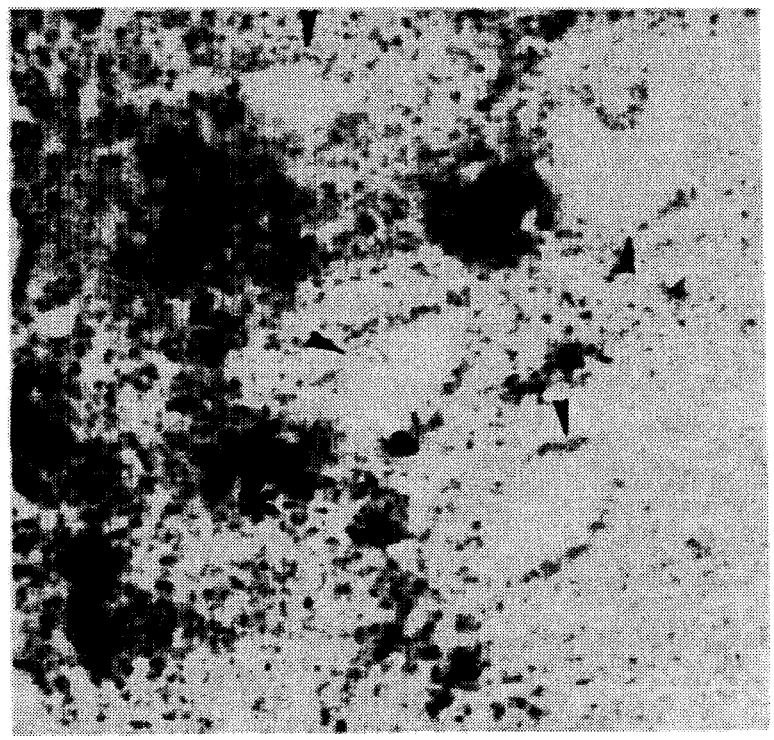
FIGS. 8A–8D display immunostaining for the $\beta_3$ subunit of the $\alpha_v\beta_3$ vitronectin receptor. Endometrial epithelial cells (arrowheads) underwent alterations in $\beta_3$ expression throughout the menstrual cycle. Samples were obtained from the proliferative phase (A), early secretory phase (B; day 18), and from the mid secretory phase (C; day 22). An endometrial biopsy from a patient with mild endometriosis (D) had no epithelial staining for $\beta_3$, despite being judged "normal, in phase day 22–23" by histologic criteria. The immunoreactions (areas of brown staining) were developed by the avidin-biotin-peroxidase complex using diaminobenzadine as a chromagen. Vascular elements (asterisks) stained positive for the $\beta_3$ subunit in all samples. For better contrast, the sections were counterstained with methyl green. Green staining signifies the absence of $\beta_3$ expression. The patterns of staining in A and B correspond to HSCOREs of 0 and in "C" to an HSCORE of 2.6. Magnification: 200X.
Figure 8B:
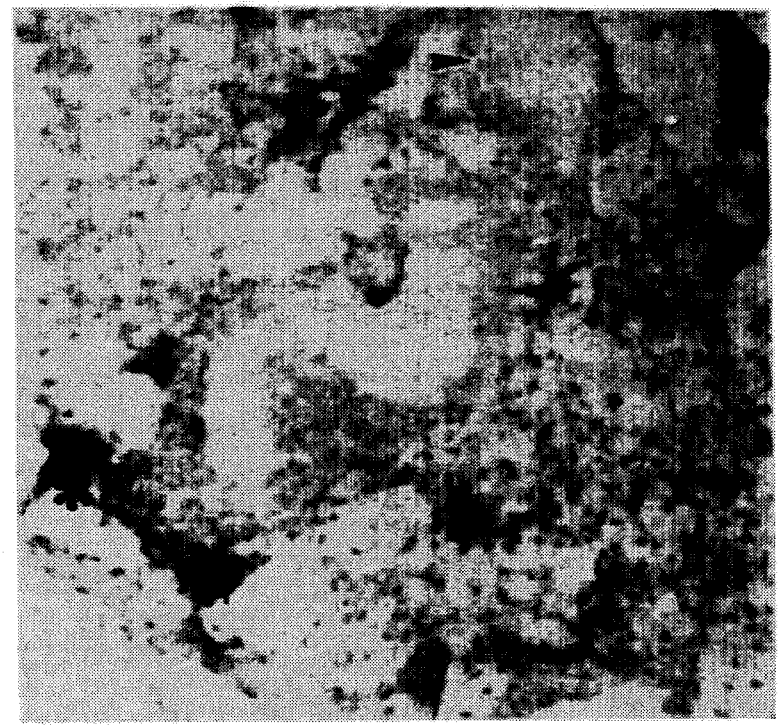
Figure 8C:
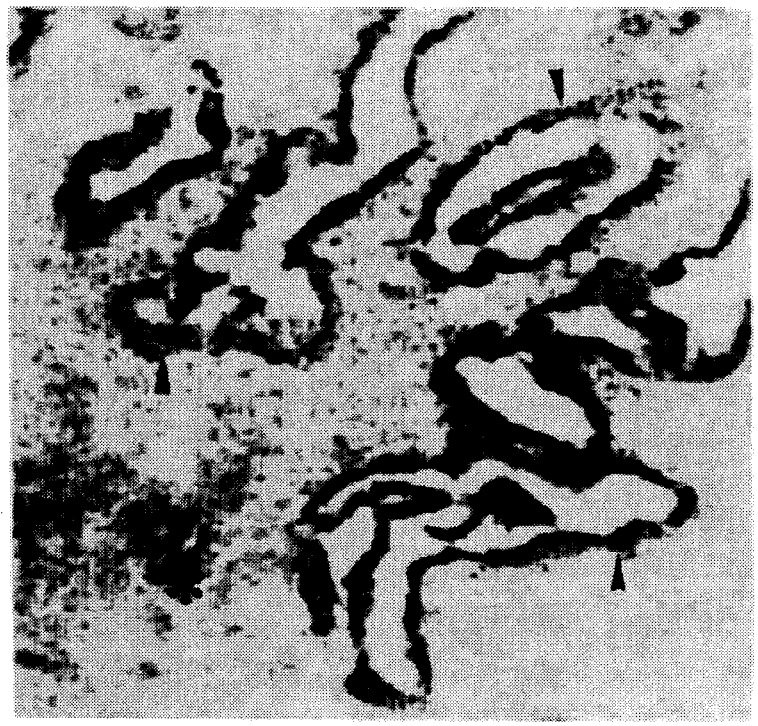
Figure 8D:
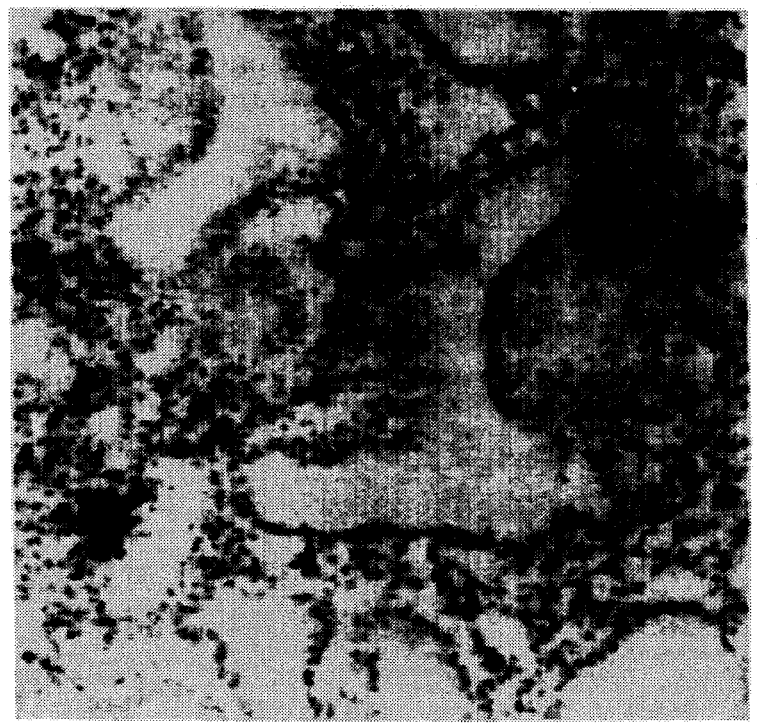

Immunostaining for endometrial $\beta_3$ was performed on each of the 268 endometrial biopsies obtained from throughout the menstrual cycle (see FIG. 7). Examples of cycle specific expression of $\beta_3$ subunit using the immunohistochemical staining are shown in FIG. 8A (proliferative), FIG. 8B (day 18), FIG. 8C (day 22) and a sample from cycle day 23 with negative staining in a patient with endometriosis whose "in phase" biopsy was read as "day 22–23" on histologic section (D). As seen in all cases, immunostaining of the vascular endothelium remains present even in samples with no epithelial staining for this integrin, thus serving as a positive internal control for the immunostaining technique. Based on the distribution of $\beta_3$ shown in FIG. 7 and the theory that the $\beta_3$ subunit is normally expressed in endometrium from day 20 and later, all samples which were histologically dated to cycle day 20 or greater were included for further evaluation (n=241). Cases with known endometriosis (102/241; 43.5%) were compared with infertile controls without endometriosis (116/241; 48.1%) and with 20 fertile controls (20/241; 83%). As listed in Table 4, both the endometriosis group and the infertile controls were younger than the fertile controls. The resulting staining was evaluated on a Nikon microscope at low (100X) and higher (400X) magnification. The HSCORE, a semiquantitative index which estimates both intensity and distribution of positive staining for $\beta_3$ integrin, was calculated using the following equation:

$$HSCORE = \Sigma Pi(i+1)$$

where i=intensity of staining with a value of 1, 2, or 3, weak, moderate, or strong, respectively, and Pi is the percentage of stained epithelial cells for each intensity, varying from 0–100%. Low intraobserver values (r=0.994; p=0.00001) in uterine tissues has been reported using this technique by Budwit-Novotny, D. A., et al., "Immunohistochemical Analyses of Estrogen Receptor in Endometrial Adenocarcinoma Using a Monoclonal Antibody", *Cancer Res.*, 1986 46:5419–5425. Examples of representative HSCOREs reflecting changing levels of staining intensity and distribution is illustrated FIGS. 8A–8D. Photomicrographs were made using Kodak 100 ASA film.

Statistical Analysis

Infertile endometriosis patients were compared to infertile controls without endometriosis and fertile controls. Comparisons were also made between nulliparous endometriosis patients and parous endometriosis patients on selected characteristics such as age and HSCORE and were performed using the nonparametric Wilcoxon text. Wilcoxon, F., Individual Comparisons by Ranking Methods. *Biometrics Bull* 1945; 1:80–85.

Receiver Operator Characteristic (ROC) analysis was used to determine the optimal cutoff value for HSCORE in women prospectively undergoing laparoscopy. Metz, C. E., Basic Principles of ROC analysis. Sem Nuclear Med 1978; 8:283–298. An HSCORE cutoff value was sought as the highest positive predictive value of endometriosis which meant seeking a high specificity at the cost of moderate sensitivity. A high positive predictive value minimizes the number of women who would otherwise undergo unnecessary surgery, using this test as a diagnostic modality for endometriosis. The HSCORE cutoff value was 0.7, which yielded a sensitivity of 38%, specificity of 91%, and a positive predictive value of 86% for the detection of endometriosis.

The association between HSCORE and endometriosis was first evaluated by a nonparametric test (Wilcoxon test) and further evaluated by multiple logistic regression in the sample of 241 women whose biopsies were histologically cycle day 20 or greater. As seen in Table 4, the mean HSCORE was significantly lower for the infertile endometriosis group (p<0.003) compared to fertile controls (p<0.002) and the infertile controls without endometriosis (p<0.012; Table 4). Interestingly, the infertile controls without endometriosis also had a borderline lower HSCORE for $\beta_3$ staining than the fertile control group (p=0.05).

TABLE 4

Demographic and HSCORE Characteristics of Subjects Whose Endometrial Biopsies Were Histologically Normal and Cycle Day 20 or Greater

|  | Infertile w/ Endometriosis n = 105 | Infertile w/o Endometriosis Infertile Controls n = 116 | Fertile Controls n = 20 |
|---|---|---|---|
| Characteristic |  |  |  |
| Age (yr) mean ± S.D. | 34.1 ± 4.1+ | 34.5 ± 4.7++ | 36.9 ± 4.9 |
| Severity AFS score |  |  |  |
| I | 40 (38.5%) |  |  |
| II | 44 (42.3%) |  |  |
| III | 15 (14.3%) |  |  |
| IV | 6 (5.8%) |  |  |
| HSCORE |  |  |  |
| Mean ± S.D. | 1.30 (±1.09)* | 1.68 (±0.95)** | 2.15 ± (0.66) |
| Median | 1.3 | 1.75 | 2.05 |
| Max | 3.6 | 3.4 | 3.6 |

+p < 0.003 vs. fertile controls, by Wilcoxon test.
++p < 0.01 vs. fertile controls, by Wilcoxon test.
*p < 0.02 vs. fertile controls and p < 0.012 versus infertile controls without endometriosis, by Wilcoxon test.
**p = 0.05 vs. fertile controls, by Wilcoxon test.

Severity of endometriosis based on AFS classification appeared to be associated with the presence or absence of the $\beta_3$ immunostaining. All 105 patients with infertility and endometriosis were stratified by severity of disease. The distribution of cases by AFS severity score is listed in Table 4. The HSCORE of the two groups based on AFS severity score, I and II (minimal and mild; n=84) versus III and IV (moderate and severe; n=21) demonstrated a significant difference using a Wilcoxon test (p=0.0151). Therefore, defective $\beta_3$ expression is specifically associated with endometriosis stages I and II.

Multiple logistic regression using EGRET was used to evaluate the association between endometriosis and HSCORE, after adjusting for the effects of age and parity status, and taking into account the potential interaction of parity taking into account the potential interaction of parity status. Mauritisen, R. EGRET. Statistics and Epidemiology Research Corporation Software. Seattle, Wash., 1990.

By multiple logistic analysis, the crude relative risk (RR) and 95% confidence interval (CI) based on a model with only HSCORE as the independent variable and the presence or absence of endometriosis as the dependent (outcome) variable, was 0.6 (0.5–0.8) when calculated for an HSCORE of 0.7 (by ROC analysis). A relative risk (RR) of 1 means there is no effect, that two groups are the same with regard to risk for endometriosis. A RR of 0.6 is highly significant, confidence intervals show the range of confidence of the test. Together, RR and CI define an increased risk of having endometriosis in nulliparous women with a HSCORE of 0.7 or less. The addition of age into the model did not change the result, but there was a statistically significant interaction with parity status (p=0.030). Accordingly, the adjusted RR (95% CI) was 0.6 (0.4–0.9) for nulliparous women compared to 1.2 (0.8–1.8) for parous women. These results indicate that the absence of $\beta_3$ (as indicated by HSCORE) in nulliparous women is a statistically significant prediction of endometriosis. Restricting the analysis to women with only minimal and mild disease did not change the result substantially. The adjusted RR (95% CI) in nulliparous women versus 0.5 (0.4–0.8) compared to 1.2 (0.7–1.8) in parous women.

Figure 9:
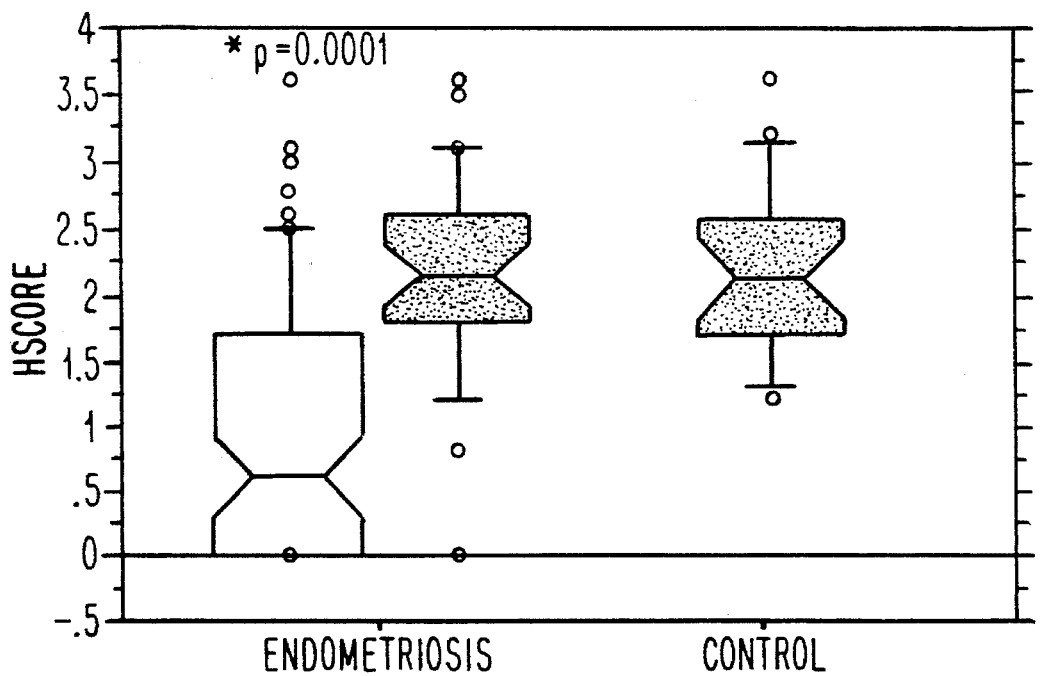
FIG. 9 is a comparison of immunostaining results for endometrial $\beta_3$ integrin in normal fertile controls (Control; n=20), infertile women with endometriosis and prior parity (Parous; n=28) and nulliparous infertile women with endometriosis (Nulliparous; n=76). The unpaired t test compares the mean of two groups and determines the likelihood of the observed difference occurring by change; the chance is reported as a p value. Using the unpaired t test, the overall HSCORE was significantly lower in the latter group compared with either of the other two. HSCORE was calculated as described.

To further examine this relationship between reproductive history and HSCORE, the 105 patients with endometriosis were stratified by parity and compared to the fertile control group (Table 5). The control population was older than the parous and nulliparous endometriosis groups. The HSCORE in the nulliparous endometriosis group was less than that of the parous endometriosis group and the fertile control group (p<0.0001, for each group), but there was no difference between the parous group with endometriosis and the fertile controls (p=0.98). The comparison between these three groups is depicted graphically in FIG. 9.

TABLE 5

Comparison between Nulliparous and Parous Women with Endometriosis and Normal Fertile controls

|  | Endometriosis Patients n = 105 | | Fertile Controls n = 20 |
|---|---|---|---|
|  | Nulliparous n = 78 | Parous n = 27 |  |
| Characteristic |  |  |  |
| Age (yr) mean ± S.D. | 34.1 ± 4.1+ | 34.3 ± 4.0++ | 36.9 ± 4.9 |
| Severity AFS score |  |  |  |
| I | 30 (38.5%) | 10 (37.0%) |  |
| II | 33 (42.3%) | 11 (40.7%) |  |
| III | 11 (14.1%) | 4 (14.8%) |  |
| IV | 4 (5.1%) | 2 (7.4%) |  |
| HSCORE |  |  |  |
| Mean ± S.D. | 1.03 (±1.04)* | 2.10 (±0.79)** | 2.15 ± (0.66) |
| Median | 0.6 | 2.1 | 2.05 |
| Max | 3.6 | 3.6 | 3.6 |

+p < 0.004 vs. fertile controls, by Wilcoxon test.
++p < 0.02 vs. fertile controls, by Wilcoxon test.
*p < 0.0001 vs. parous endometriosis patients and p < 0.0001 versus fertile controls, by Wilcoxon test.
**p < 0.98 vs. fertile controls, by Wilcoxon test.

The observation that differences in integrin expression correlated with the diagnosis of endometriosis, prompted the evaluation of the usefulness of this marker in predicting this disorder in women prospective to the diagnostic laparoscopy. As a subgroup of the original 241 samples, 89 biopsies were obtained prospectively prior to diagnostic laparoscopy. Chronological dating was established by urinary luteinizing hormone, LH, surge and/or the onset of the next menstrual period. Endometrial dating was performed using the criteria of Noyes et al., "Dating the Endometrium", *Fertil. Steril.* 1950, 1:3. All 89 of these women subsequently underwent diagnostic laparoscopy to establish the presence or absence of endometriosis. The severity of the disease, when present, was staged according to the revised American Fertility Society, AFS, criteria set forth in American Fertility Society: Revised American Fertility Society classification of endometriosis, supra. The surgeons performing the diagnostic laparoscopies were blinded with regard to the result of the immunohistochemical findings. Likewise the interpretation of the biopsy results (estimation of $\beta_3$ expression) was done in a blinded fashion using HSCORE, which estimates both intensity and distribution of positive staining for $\beta_3$ integrin. The 0.7 HSCORE value, determined as the optimal cutoff, yielded a sensitivity of 38%, a specificity of 91% and the highest positive predictive value of 86% for the prospective detection of endometriosis. Overall, 50 patients were prospectively found at laparoscopy to have endometriosis at a variety of AFS stages. Negative staining, indicating no $\beta_3$ expression, based on ROC analysis, was detected in 22 samples. Of these 22 patients without $\beta_3$ staining, 19 were found to have endometriosis. ROC analysis was performed to establish the optimal cutoff value for normal samples. To the best of Applicant's knowledge, the present invention is the first non-surgical test that has been demonstrated to predict the presence of minimal or mild endometriosis.

All patients subsequently found to have endometriosis were not missing the $\beta_3$ subunit. The present invention identifies a subgroup of infertility patients with a deficit in $\beta_3$ which characterizes women with defective uterine receptivity. This association between endometriosis and defective $\beta_3$ integrin expression may represent the first cycle-specific defect during the putative window of implantation. Detecting the loss of $\beta_3$ may signify patients with endometriosis who are most at risk for infertility due to an endometrial factor. While implantation may be the result of a cascade of different molecules, the present invention reveals the loss of a single component may be sufficient to explain a failure of implantation.

The present invention reveals the loss of $\beta_3$, normally expressed at the initiation of the window of implantation, is associated with women who appear to be the most infertile. Prospective use of this marker protein has demonstrated that the $\beta_3$ integrin subunit is a useful test with a high specificity and positive predictive value for the nonsurgical diagnosis of minimal or mild endometriosis. As a potential marker of uterine receptivity that may predict fertility potential, the study of this subgroup of infertility patients allows greater refinement of diagnosing this enigmatic disease.

Determination of Endometriosis in the Infertile Patient Population

Biopsies will be obtained from throughout the menstrual cycle from women being evaluated for infertility. Women who are parous and nulliparous will be included in the study. The biopsies will be screened for participation in a study based upon criteria including accurate knowledge of menstrual cycle day or "in phase" histology and freedom from menstrual cycle disturbances (anovulation (suspension or cessation of ovulation), perimenopausal state (dysfunctional uterine bleeding), luteal phase defect (histologic evidence of maturational delay of the endometrium), the presence or use of an intrauterine device or endometritis (inflammation of endometrium due to infectious agents or chemical irritation). Patients with endometrial hyperplasia (an increase in the number of cells in endometrium), neoplasia (a pathologic process resulting in formation or growth of abnormal tissue or tumors, benign or malignant), those on hormonal therapy (including oral contraceptives, estrogen replacement therapy and progestens), and those with luteal phase deficiency will be excluded.

Endometrial biopsies will be obtained after day 19 (post ovulatory day 6 or greater) based on urinary luteinizing hormone, LH, surge or next menstrual period, a time in the menstrual cycle when epithelial $\beta_3$ is expressed, Lessey, et al., supra. Fertile and infertile controls will also be selected.

Immunoperoxidase staining will be performed on the patient samples as described by Lessey, et al., supra. Briefly, immunoperoxidase staining will be performed on cryostat sections of endometrium throughout the menstrual cycle. Serial cryosections 4–8 μ thick will be placed onto poly-L lysine coated slides, fixed in −20° C. acetone for 10 minutes, and stained using Vectastain Elite® ABC kits (Vector Laboratories, Burlingame, Calif.). Diaminobenzadine (DAB; Sigma Chemical Co., St. Louis, Mo.) will be used as the chromogen. Primary antibody consisting of SSA6 (specific to the $\beta_3$ subunit of the vitronectin receptor) will be placed on cryosections following blocking with 1% bovine serum albumin in phosphate buffered saline, PBS, and allowed to bind at room temperature for 1 hour. A PBS rinse, pH 7.2 to 7.4, will be followed by secondary antibody consisting of biotinylated goat anti-mouse antibody for 30 minutes. Following PBS rinse, the endogenous peroxidases will be quenched with a 30 minute incubation with 0.3% $H_2O_2$ in absolute ethanol, followed by a 30 minute rehydration in PBS. Avidin: biotinylated horseradish peroxidase macromolecular complex (ABC) will then be incubated on the sections for 30 minutes before adding diaminobenzadine for 3 minutes to complete the reaction. Samples will be subsequently washed in PBS and mounted.

The HSCORE and statistical analysis, using Wilcoxon test, ROC analysis, and p values, for infertile females is expected to be similar to that of nulliparous infertile females set forth above. HSCORE cutoff value, sensitivities and specificities values will be determined for the detection of endometriosis in infertile patients. The patients will also be separated as to severity of endometriosis based on AFS classification. EGRET will be used to evaluate the association between endometriosis and HSCORE, after adjusting for the effects of age and parity status, supra. Crude relative risk and confidence intervals will be calculated for endometriosis. Overall, it is expected that integrin expression, detected by the absence of $\beta_3$, will correlate with the diagnosis of endometriosis in infertile females.

Various modifications of the invention in addition to those shown and described herein will be apparent to those skilled in the art from the foregoing description. Such modifications are also intended to fall within the scope of the appended claims.

What is claimed:

1. A method for screening for endometriosis comprising:
   a. obtaining a sample of endometrium selected from menstrual cycle day 20 to 24 from a patient free from luteal phase defect,
   b. identifying said sample of endometrium as nulliparous,
   c. contacting said sample with a monoclonal antibody specific for $\beta_3$ integrin,
   d. assaying for $\beta_3$ integrin in said sample, and e. correlating the absence of $\beta_3$ integrin expression with endometriosis, wherein said endometriosis is mild/minimal endometriosis, thereby predicting endometriosis.

2. The method of claim 1 wherein said monoclonal antibody is SSA6.

3. The method of claim 1 wherein said $\beta_3$ is combined with another integrin subunit.

4. The method of claim 3 wherein said other integrin subunit is $\alpha_v$.

5. The method of claim 4 wherein said monoclonal antibody is 23C6.

6. The method of claim 1 wherein said $\beta_3$ is detected by immunohistochemically staining said sample of endometrium contacted with said monoclonal antibody specific for $\beta_3$.

7. The method of claim 1 wherein said $\beta_3$ is detected by immunoblotting $\beta_3$ from said sample of endometrium contacted with said monoclonal antibody specific for $\beta_3$.

8. The method of claim 1 wherein said endometrium is human.

* * * * *